(12) United States Patent
Obata et al.

(10) Patent No.: US 6,717,092 B2
(45) Date of Patent: Apr. 6, 2004

(54) METHOD OF MANUFACTURING TREATMENT INSTRUMENT OF ENDOSCOPE

(75) Inventors: Yoshihiro Obata, Saitama-ken (JP);
Kikuo Iwasaka, Saitama-ken (JP);
Shinichi Matsuno, Kanagawa-ken (JP);
Hajime Yoshino, Saitama-ken (JP);
Akira Sugiyama, Kanagawa-ken (JP);
Hidehito Kurosawa, Tokyo (JP);
Shigeru Ogawa, Saitama-ken (JP);
Hideo Nanba, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 0 days.

(21) Appl. No.: 09/923,357

(22) Filed: Aug. 8, 2001

(65) Prior Publication Data

US 2002/0017515 A1 Feb. 14, 2002

(30) Foreign Application Priority Data

| Aug. 11, 2000 | (JP) | 2000-244491 |
| Sep. 1, 2000 | (JP) | 2000-265124 |
| Oct. 27, 2000 | (JP) | 2000-328675 |
| Oct. 27, 2000 | (JP) | 2000-328911 |
| Oct. 27, 2000 | (JP) | 2000-329039 |
| Nov. 30, 2000 | (JP) | 2000-365831 |
| Dec. 22, 2000 | (JP) | 2000-391556 |
| Dec. 22, 2000 | (JP) | 2000-391659 |

(51) Int. Cl.$^7$ .......................... B23K 31/02; B23K 9/007
(52) U.S. Cl. ........................ 219/61; 219/127
(58) Field of Search ................. 600/133, 155, 600/139, 140, 144, 146; 219/127, 61

(56) References Cited

U.S. PATENT DOCUMENTS

| 2,050,416 A | * | 8/1936 | Blanchard | 219/121.11 |
| 3,035,158 A | * | 5/1962 | Copleston et al. | 219/127 |
| 4,256,948 A | * | 3/1981 | Wolf et al. | 101/93.05 |
| 4,308,446 A | * | 12/1981 | Okane et al. | 219/123 |
| 4,986,257 A | * | 1/1991 | Chikama | 600/146 |
| 5,094,647 A | * | 3/1992 | Courtney | 2/104 |
| 5,782,848 A | * | 7/1998 | Lennox | 600/569 |
| 5,882,293 A | * | 3/1999 | Ouchi | 600/104 |
| 5,904,647 A | * | 5/1999 | Ouchi | 600/104 |
| 6,093,155 A | * | 7/2000 | Ouchi | 600/569 |
| 6,133,540 A | * | 10/2000 | Weiss et al. | 219/56 |
| 6,375,650 B1 | * | 4/2002 | Ouchi | 600/139 |
| 6,403,921 B1 | * | 6/2002 | Maeda et al. | 219/125.11 |

FOREIGN PATENT DOCUMENTS

| JP | 61038326 A | * | 2/1986 |
| JP | 1-242053 | * | 9/1989 |
| JP | 04327369 A | * | 11/1992 |
| JP | 5-3852 | | 1/1993 |
| JP | 7-13692 | * | 4/1995 |
| JP | 8-146306 | | 6/1996 |

* cited by examiner

Primary Examiner—M. Alexandra Elve
Assistant Examiner—Kevin McHenry
(74) Attorney, Agent, or Firm—Greenblum & Bernstein, P.L.C.

(57) ABSTRACT

A treatment instrument includes a first coil and a second coil that is different from said first coil. The first and second coils are connected to each other. An operation wire is inserted in the first and second coils, and a tip end of the wire is connected to a treatment device. Upon movement of the wire, the treatment device operates. A method of manufacturing such a treatment instrument includes inserting one end of the first coil and one end of the second coil in a connection pipe from opposite ends thereof, exposing both ends of the connection pipe and corresponding portions of the first and second coils. The portions exposed to the arc columns are melted and connected.

34 Claims, 32 Drawing Sheets

METHOD OF MANUFACTURING TREATMENT INSTRUMENT OF ENDOSCOPE

BACKGROUND OF THE INVENTION

The present invention relates to a method of manufacturing a treatment instrument of an endoscope, and more particularly to a method of manufacturing which includes a step of connecting parts of the treatment instrument of the endoscope.

Most of the treatment instruments of an endoscope has a connected portions. For example, an instrument having an operation wire and forceps to be operated, there is a portion where an end of the wire is connected to a mechanism for moving the forceps. For another example, an instrument may have a portion to be bent easily and a portion which is formed to be relatively rigid. Such portions may be formed with coils made of thin wires and thick wires, respectively, and the flexible and rigid portions are soldered.

The soldered connection has, however, various disadvantages. For example, residual flux may corrode the coils, or when the coils are soldered, a positional relationship between the coils may change.

Japanese Utility Model Publication HEI 07-13692 disclosed a connecting structure in which a proximal end of a coil and a distal end of another coil are heat-melted by a laser beam, and then the melted portions are connected. In such a method, however, since the laser beam is used, the proximal end of one coil and the distal end of the other coil should contact without a clearance so that the laser beam does not leak therefrom. For this purpose, the end surfaces should be made flat by grinding, which requires an extra working process.

Another type of instrument is a brush instrument such as a cleaning brush for cleaning the instrument channel of the endoscope or a cytological brush for collecting tissues in the human cavity. The brush instrument includes an operation wire and a brush unit secured to the tip of the operation wire. Generally, the brush unit is made of synthetic resin, while the wire is made of metal. Since such a brush instrument is to be inserted through the instrument channel of the endoscope or human tissues, a collar is provided at the tip of the operation wire. Typically, the collar is fixed on the wire using solder, and sometimes a sufficient amount of the solder is provided to round the edges of the collar.

Since the collar is secured to the wire by soldering, residual flux may corrode the wire. Further, since the brush unit is formed of the synthetic resin, in order to avoid overheating of the brush unit, the soldering process should be done within a relatively short period of time, which sometimes makes it difficult to firmly secure the collar to the tip of the wire.

SUMMARY OF THE INVENTION

In view of the above, it is therefore an object of the present invention to provide an improved method of manufacturing treatment instrument of an endoscope, in which parts of the treatment instrument can be connected with a relatively simple method, without the disadvantages as above.

Another object of the invention is to provide a method of manufacturing instrument of an endoscope, in which the tip of a wire which is to be moved in the axial direction thereof is processed so as not to scratch or hurt the instrument channel of the endoscope, or human tissues.

According to an aspect of the invention, there is provided a method of manufacturing a treatment instrument of an endoscope, the treatment instrument including a first coil and a second coil that is different from the first coil and to be connected to the first coil, an operation wire, and a device secured to a distal end of the first coil, the wire being inserted through the first coil and the second coil, a distal end of the wire being connected to the device, the device being driven by the wire when the wire being moved in the first coil and the second coil. Such a method includes inserting one end of the first coil and one end of the second coil in a connection pipe from opposite ends thereof, and exposing ends of the connection pipe and portions of the first coil and the second coil corresponding to the ends of the connection pipe to arc columns, respectively. The portions exposed to the arc columns are melted, and thereafter, solidified.

Optionally, an outer diameter of the connection pipe member may be substantially the same as an outer diameter of the first coil outside the connection pipe and an outer diameter of the second coil outside the connection pipe, and an inner diameter of the connection pipe member may be substantially the same as an outer diameter of the first coil inside the connection pipe and an outer diameter of the second coil inside the connection pipe.

Further optionally, a plurality of positions, along a circumferential direction, of a portion where an end of the connection pipe is to be connected to the first coil are exposed to arc columns, respectively, and a plurality of positions, along a circumferential direction, of a portion where an other end of the connection pipe is to be connected to the second coil may be exposed to arc columns, respectively.

Still optionally, the connection pipe may be formed with a plurality of through holes, each of which is exposed to an arc column. With such a structure, an edge portion of each of the through holes and one of the first and second coils located at each of the through holes are heated and melted.

According to another aspect of the invention, there is provided another method of manufacturing a treatment instrument of an endoscope. The treatment instrument may include a first coil and a second coil that is different from the first coil and to be connected to the first coil, an operation wire, and a treatment device secured to a distal end of the first coil. The wire may be inserted through the first coil and the second coil, a distal end of the wire being connected to the treatment device. The treatment device can be driven by the wire when the wire is moved in the first coil and the second coil. The method includes generating an arc column between a contact portion where a proximal end side of the first coil and a distal end side of the second coil contact with each other and an electrode located in the vicinity of the contact portion, the proximal end side of the first coil and the distal end side of the second coil located at the contact portion being melted as exposed to the arc column, and solidified as cooled.

Optionally, a plurality of positions, along a circumferential direction, of the contact portion are exposed to arc columns, respectively.

Further optionally, the first coil may include a flexible coil, and wherein the second coil includes a rigid coil.

According to another aspect of the invention, there is provided a further method of manufacturing a treatment instrument of an endoscope. The treatment instrument may includes a first guide coil, an operation wire, and a device to be operated, the wire being inserted through the first guide coil, a distal end of the wire being connected to the device, the device being driven by the wire when the wire being moved in the first guide coil. The method may include inserting the first guide coil into a first cover coil, and exposing a plurality of portions of the first cover coil at positions where the first cover coil covers the first guide coil to arc columns, respectively. In this case, the first cover coil and the first guide coil at portions exposed to the arc columns can be melted, and thereafter, solidified.

Optionally, the exposing includes locating an electrode at each of the plurality of portions, and applying a predetermined voltage between the first cover coil and the electrode to generate the arc column therebetween.

Still optionally, the instrument may be a biopsy forceps having a pair of cups that is opened/closed by operation of the operation wire.

According to a further aspect of the invention, there is provided a method of manufacturing an endoscope. The endoscope may include a first guide coil, and an operation wire, the wire being inserted through the first guide coil, a distal end portion of the endoscope being provided with a moving mechanism, a distal end of the wire being connected to the moving mechanism, the moving mechanism being driven by the wire when the wire being moved in the first guide coil. The method may include inserting the first guide coil into a first cover coil, and exposing a plurality of portions of the first cover coil at positions where the first cover coil covers the first guide coil to arc columns, respectively. The first cover coil and the first guide coil at portions exposed to the arc columns can be melted, and thereafter, solidified.

Optionally, the exposing includes locating an electrode at each of the plurality of portions, and applying a predetermined voltage between the first cover coil and the electrode to generate the arc column therebetween.

According to another aspect of the invention, there is provided a further method of manufacturing an endoscope, which includes an insertion tube to be inserted in a human cavity, a bendable unit provided on a distal end side of the insertion unit, the bendable unit being operated by a pair of operation wires, and a connection member that connects the insertion tube with the bendable unit, the connection member having substantially a cylindrical shape. The method may include positioning a guide coil that covers the operation wire to elastically reinforce so that a bendable unit side end of the guide coil contacts an inner surface of the connection member, and exposing the connection member to an arc column so that the connection member and the outer surface of the guide coil being heated and melted.

Optionally, at least one through hole is formed on a side surface of the connection member. The at least one though hole may include a plurality of through holes, which are aligned in a axial direction of the connection member. Further, the exposing includes positioning a tip end portion of the guide coil at the at least one through hole, and exposing the at least one through hole to an arc column to melt the connection member and the guide coil at a position corresponding to the at least one through hole.

Further, the exposing may include connecting an electrode to the guide coil, located another electrode in the vicinity of at least one of the though holes, and applying a predetermined voltage between the electrode and the another electrode to generate an arc column therebetween.

According to a furthermore aspect of the invention, there is provided a method of manufacturing a brush instrument for an endoscope. The brush instrument may include a brush unit and an operation wire, the brush unit being secured to a distal end portion of the operation wire. Such a method may include heating a tip of the wire so that the tip of the operation wire is melted, a substantially hemispherical portion being formed thereat, and cooling the melted portion of the operation wire.

Optionally, the heating may include exposing the tip of the operation wire with an arc column. Alternatively, the heating may includes exposing the tip of the operation wire with a laser beam.

According to another aspect of the invention, there is provided a further method of manufacturing a brush instrument for an endoscope. The brush instrument may include a brush unit and an operation wire, the brush unit being secured to a distal end portion of the operation wire. The method includes inserting a tip end of the operation wire in a collar member, the operation wire protruding from the end of the collar by a predetermined amount, heating the tip of the operation wire protruding from the collar so that the tip of the operation wire is melted, a substantially hemispherical portion being formed by the melted portion of the operation wire, and cooling the melted portion of the operation wire.

The heating may include exposing the tip of the operation wire with an arc column. Alternatively, the heating may include exposing the tip of the operation wire with a laser beam.

According to a further aspect of the invention, there is provided another method of manufacturing a treatment instrument for an endoscope. The instrument includes an operable member protruded from the distal end of the endoscope, the operable member being driven by moving an operation wire inserted in the endoscope. The method may include securing the operable member onto a support member that restrict movement of the operable member, covering the operation wire with a coil, and connecting the tip end of the coil and the supporting member in accordance with arc welding.

Optionally, the supporting member may have a cylindrical portion, inner diameter of the cylindrical portion being substantially the same as an outer diameter of the coil, and the arc welding may be performed with inserting the tip of the coil in the cylindrical portion.

Further, the cylindrical portion may be formed with at least one through hole pierced in a radial direction, and wherein the tip end portion of the coil and the supporting member are connected by welding at a position where the at least one through hole is formed.

Furthermore, the at least one through hole may include a plurality of through holes distributed in a circumferential direction.

In a particular case, the treatment instrument may be a forceps provided with a pair of forceps cups.

According to a further aspect of the invention, there is provide a method of manufacturing a treatment instrument for an endoscope. The treatment instrument may include a treatment unit and an operation wire, the treatment unit being secured to a distal end portion of the operation wire, the wire being covered with a coil. The method may include heating a tip of the wire so that the tip of the operation wire and tip of the coil are melted and connected, and cooling the melted portion of the operation wire and the coil.

Optionally, the heating may include exposing the tip of the operation wire and coil with an arc column. Alternatively, the heating may include exposing the tip of the operation wire and coil with a laser beam.

In a particular case, the treatment unit may include a brush unit.

According to another aspect of the invention, there is provided a method of manufacturing a treatment instrument for an endoscope. The treatment instrument includes a treatment unit and an operation wire, the treatment unit being secured to a distal end portion of the operation wire, the wire being covered with a coil at a portion on a proximal end side with respect to the treatment unit. The method may include widening a pitch of the coil at a position a predetermined length spaced from the tip end of the coil to form an interstice portion, heating the coil and the wire at the interstice portion so that the coil and the corresponding portion of the operation wire are melted and connected, and cooling the melted portion of the operation wire and the coil.

Optionally, the heating includes exposing the interstice portion of the coil and the corresponding position of the operation wire with an arc column.

Alternatively, the heating may include exposing the interstice portion of the coil and the corresponding position of the operation wire with a laser beam.

In a particular case, the treatment unit may include a brush unit.

BRIEF DESCRIPTION OF THE EMBODIMENTS

Figure 1:
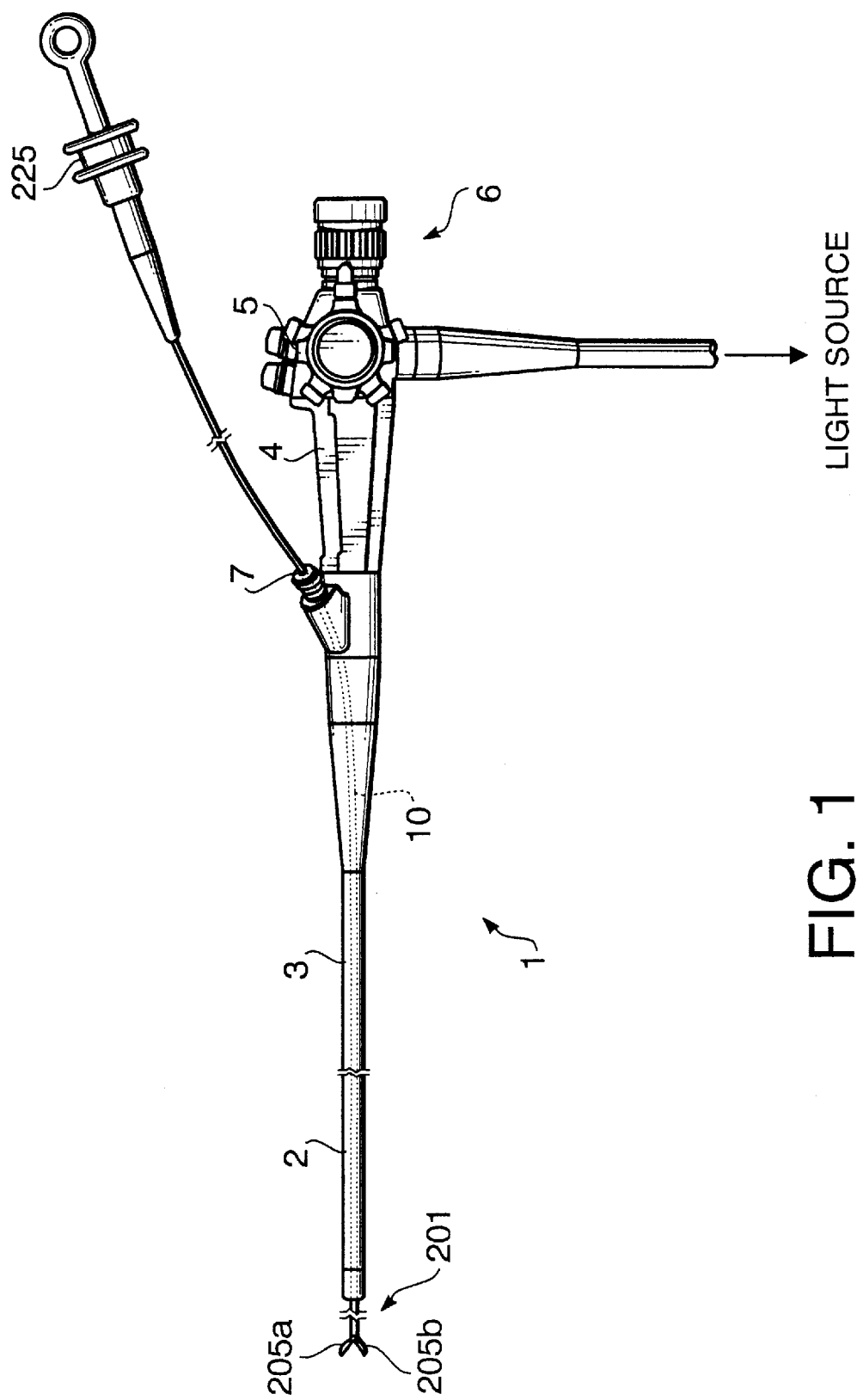
FIG. 1 shows an endoscope to which a biopsy forceps is implemented.
Figure 2:
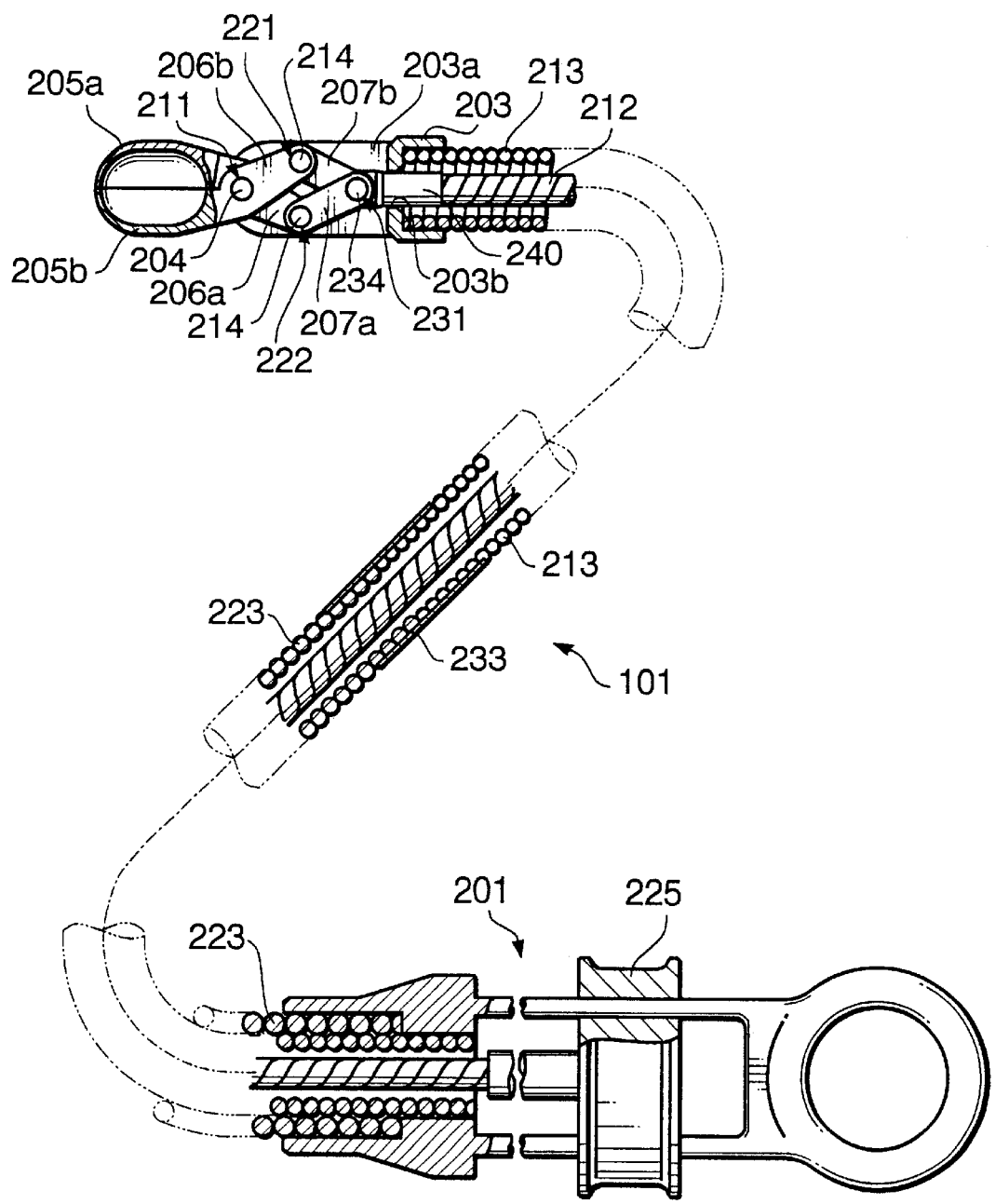
FIG. 2 shows a cross section of a part of the biopsy forceps.
Figure 5:
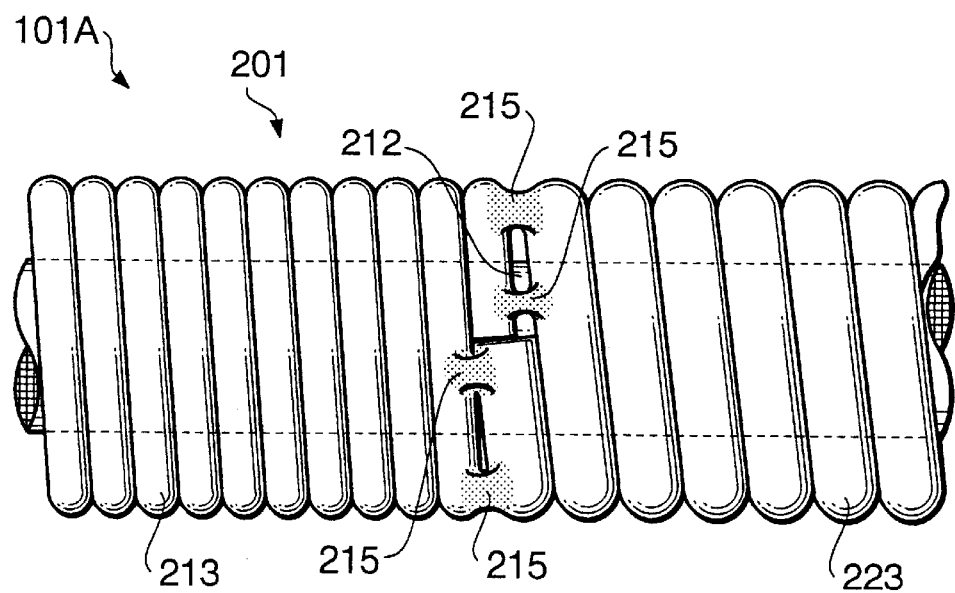
Figure 6:
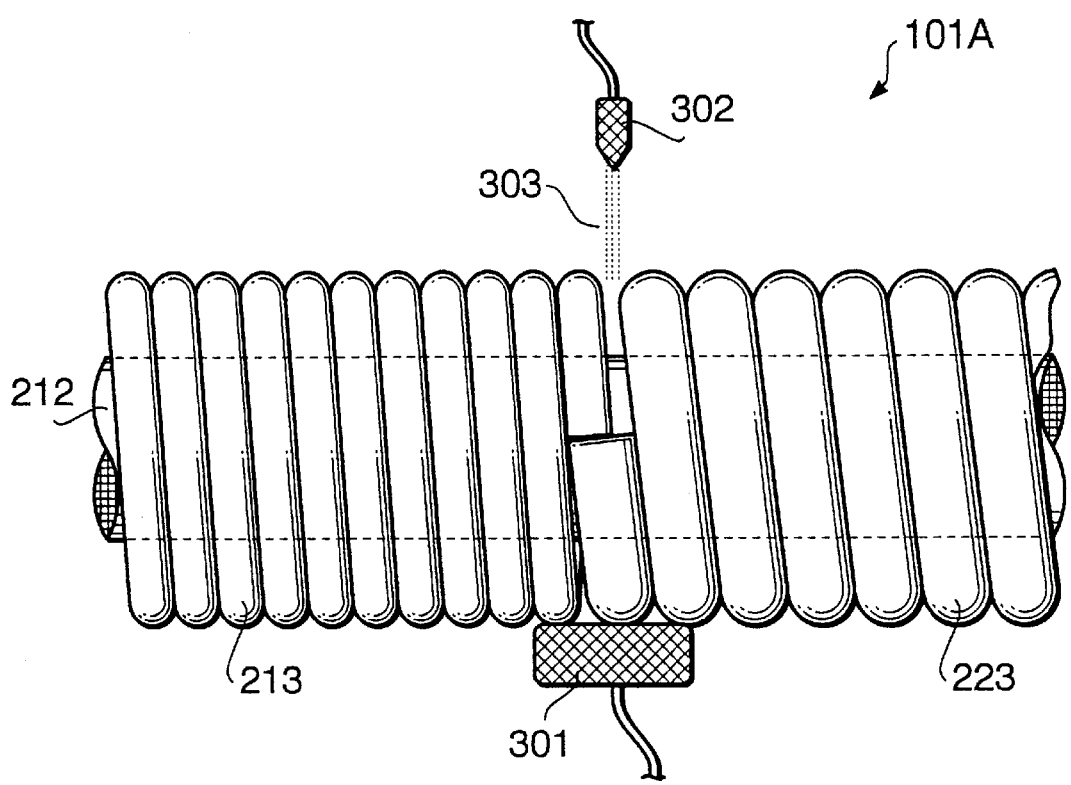
Figure 7:
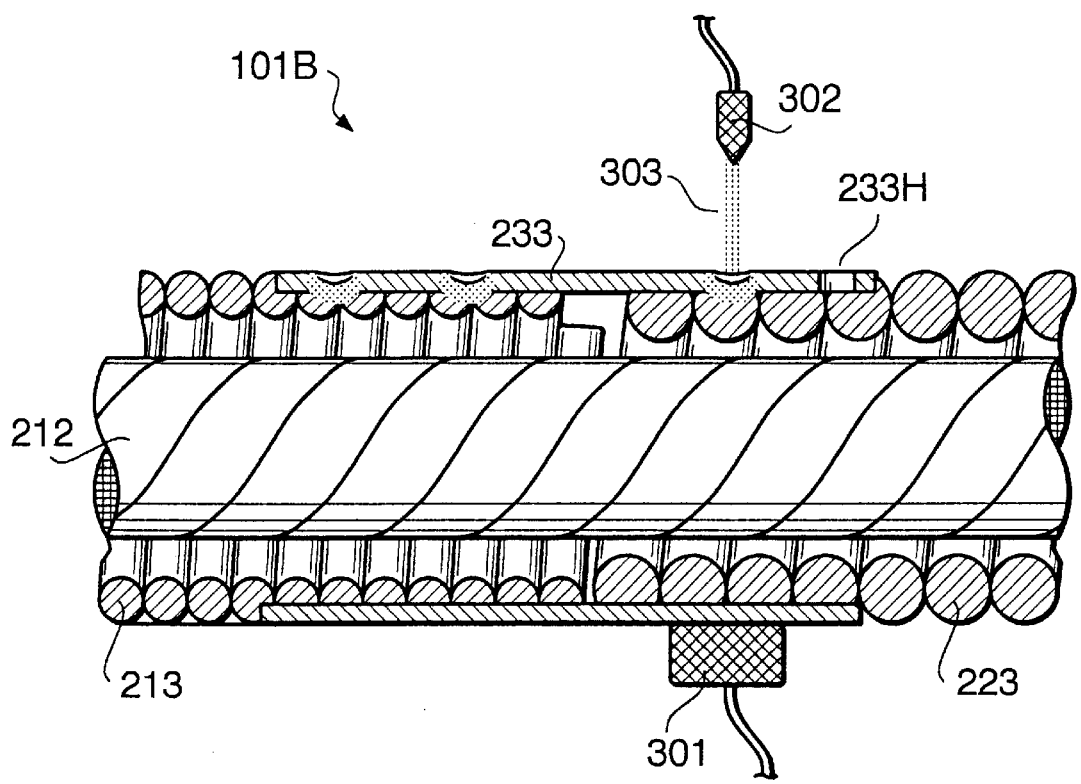
Figure 8:
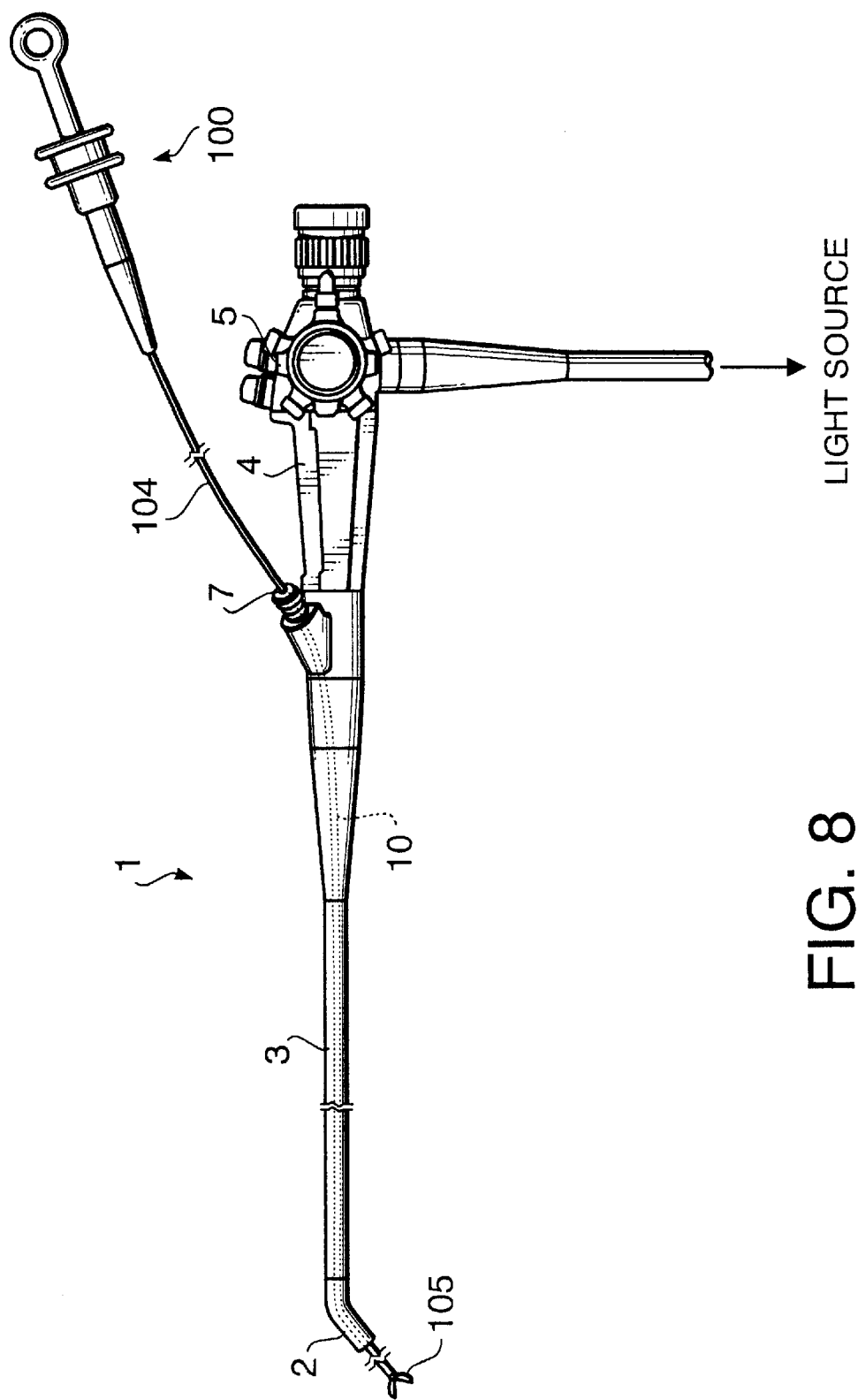
Figure 9:
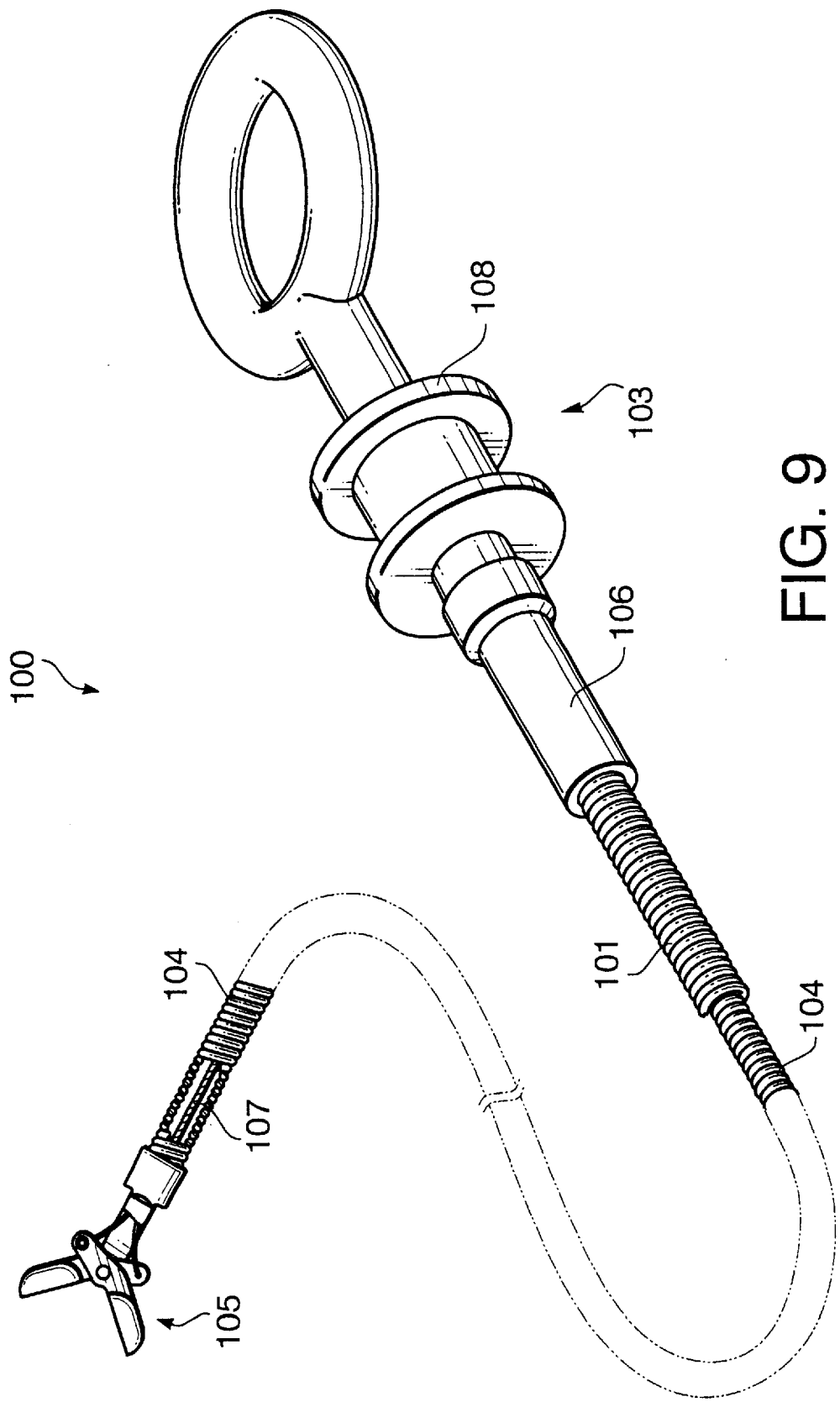
Figure 10:
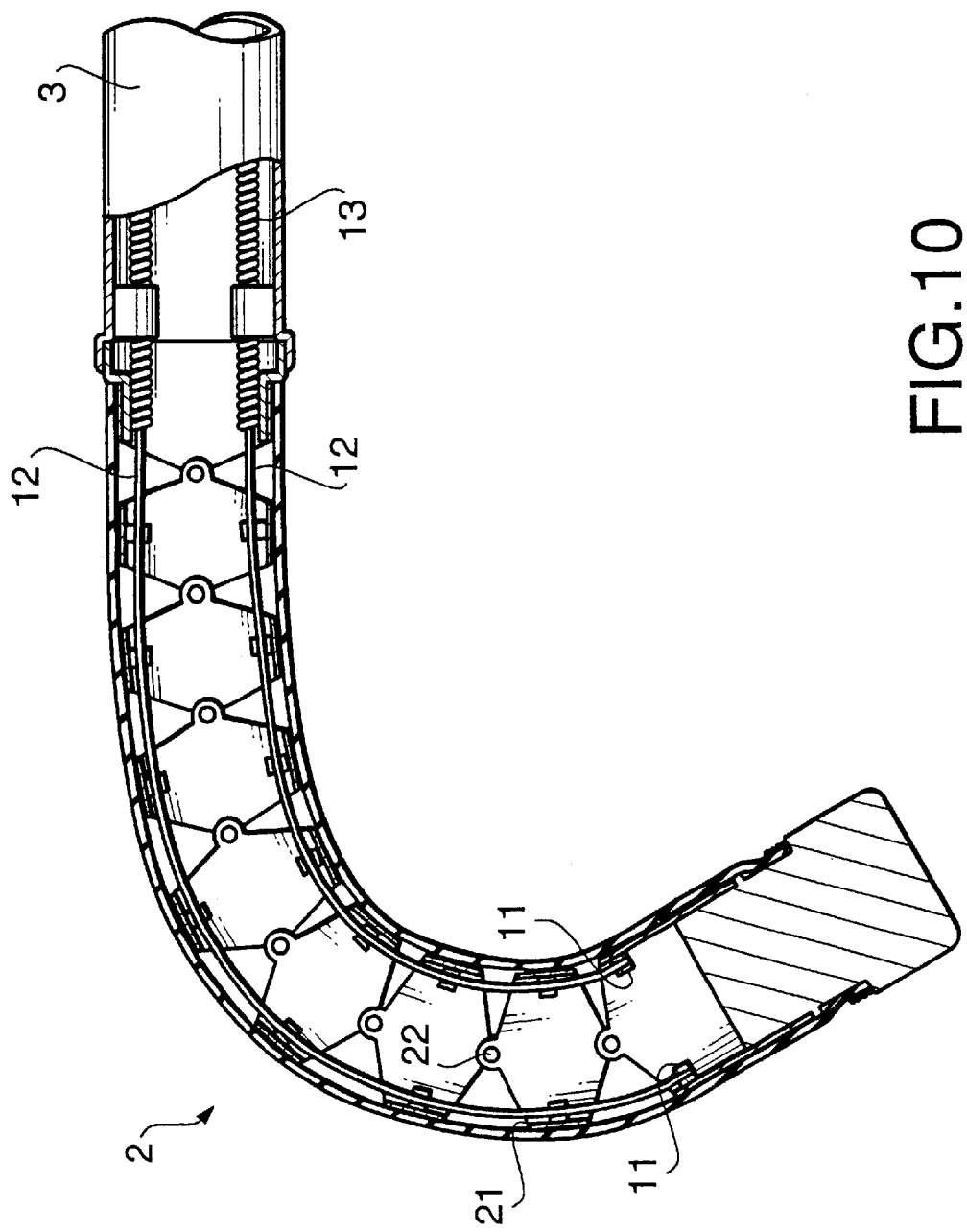
Figure 11:
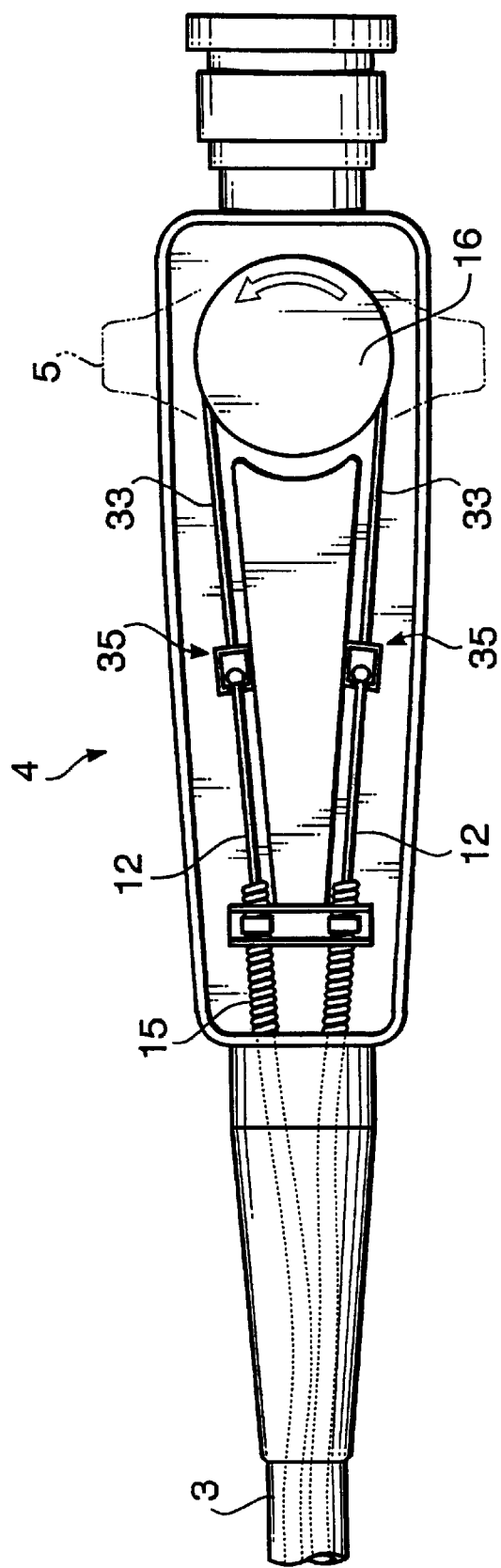
Figure 12:
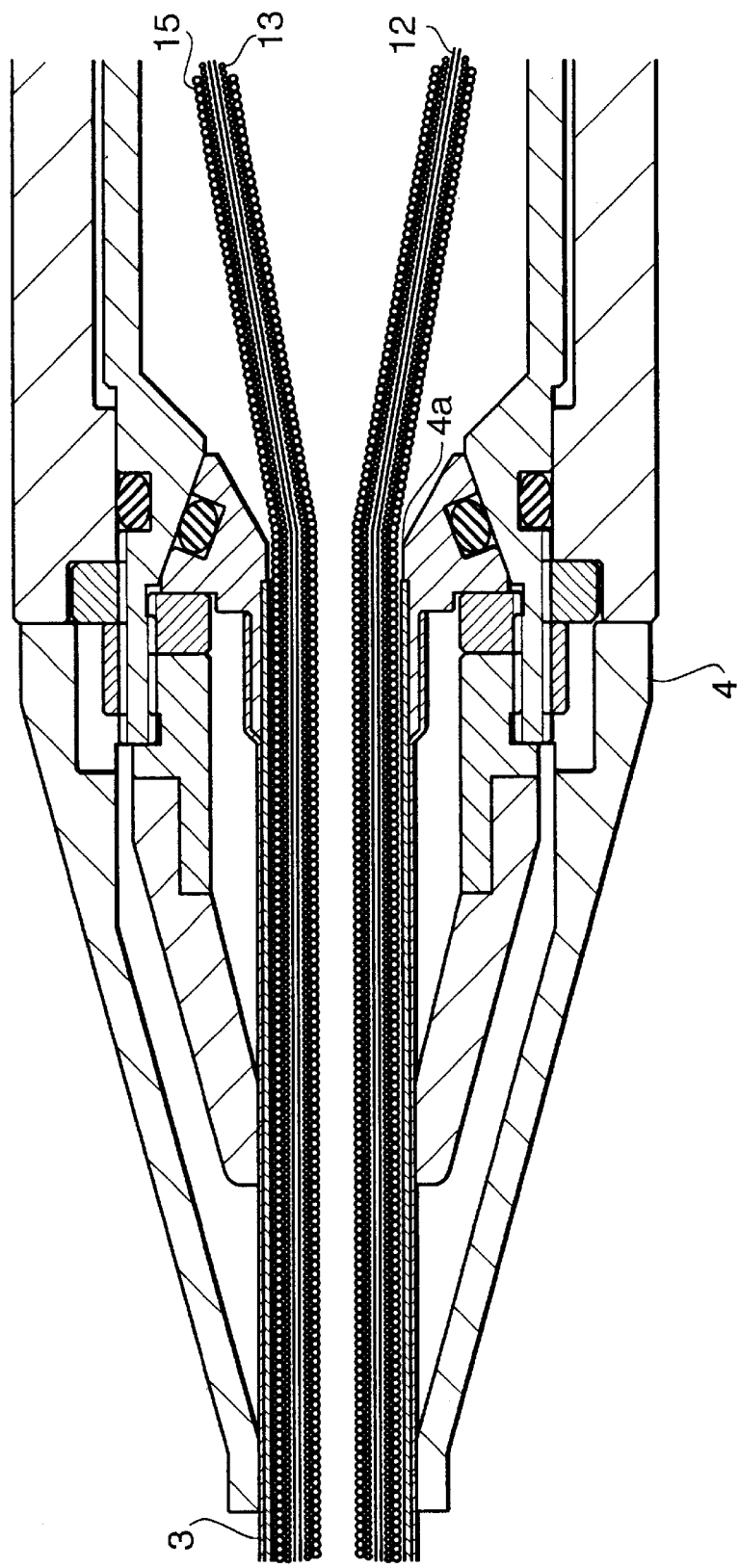
Figure 13:
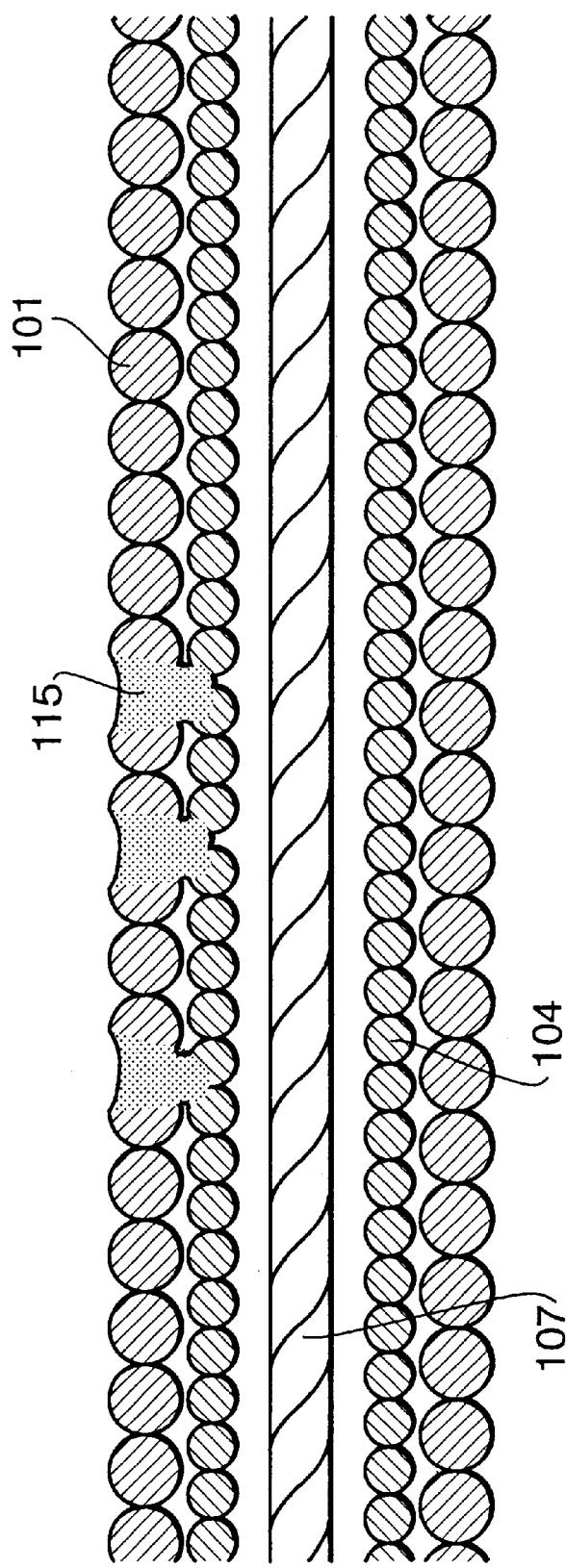
Figure 14:
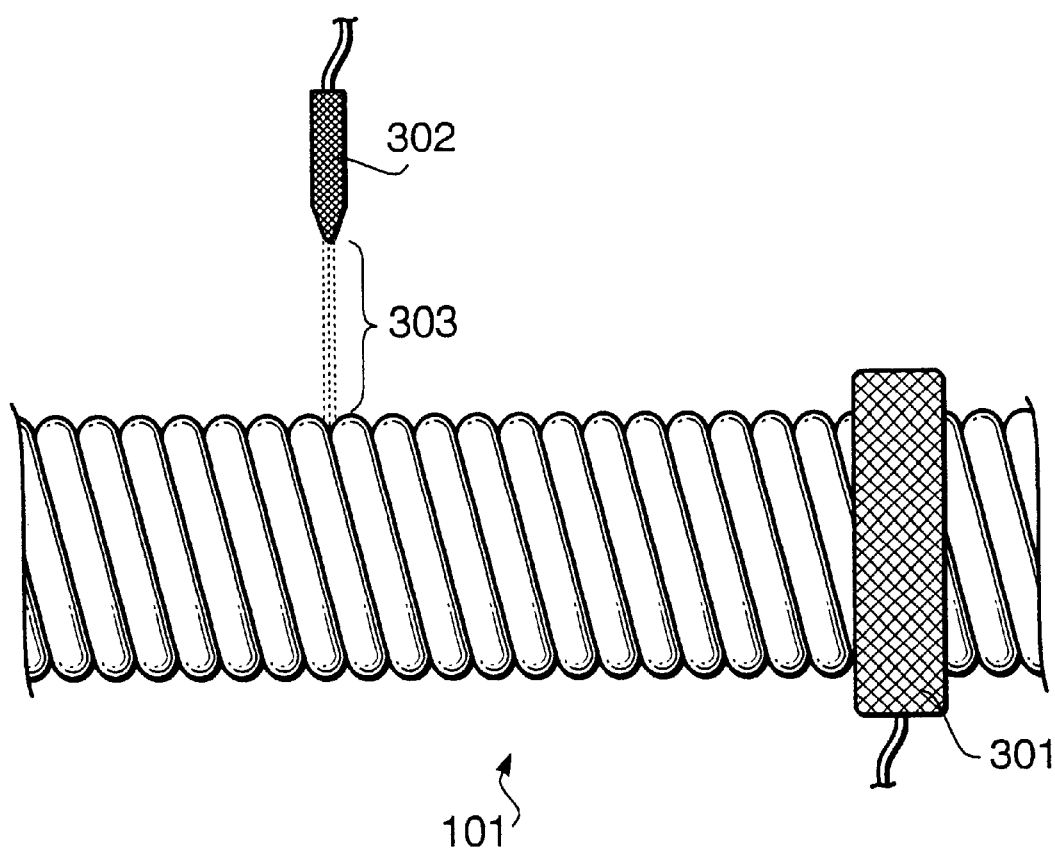
Figure 15:
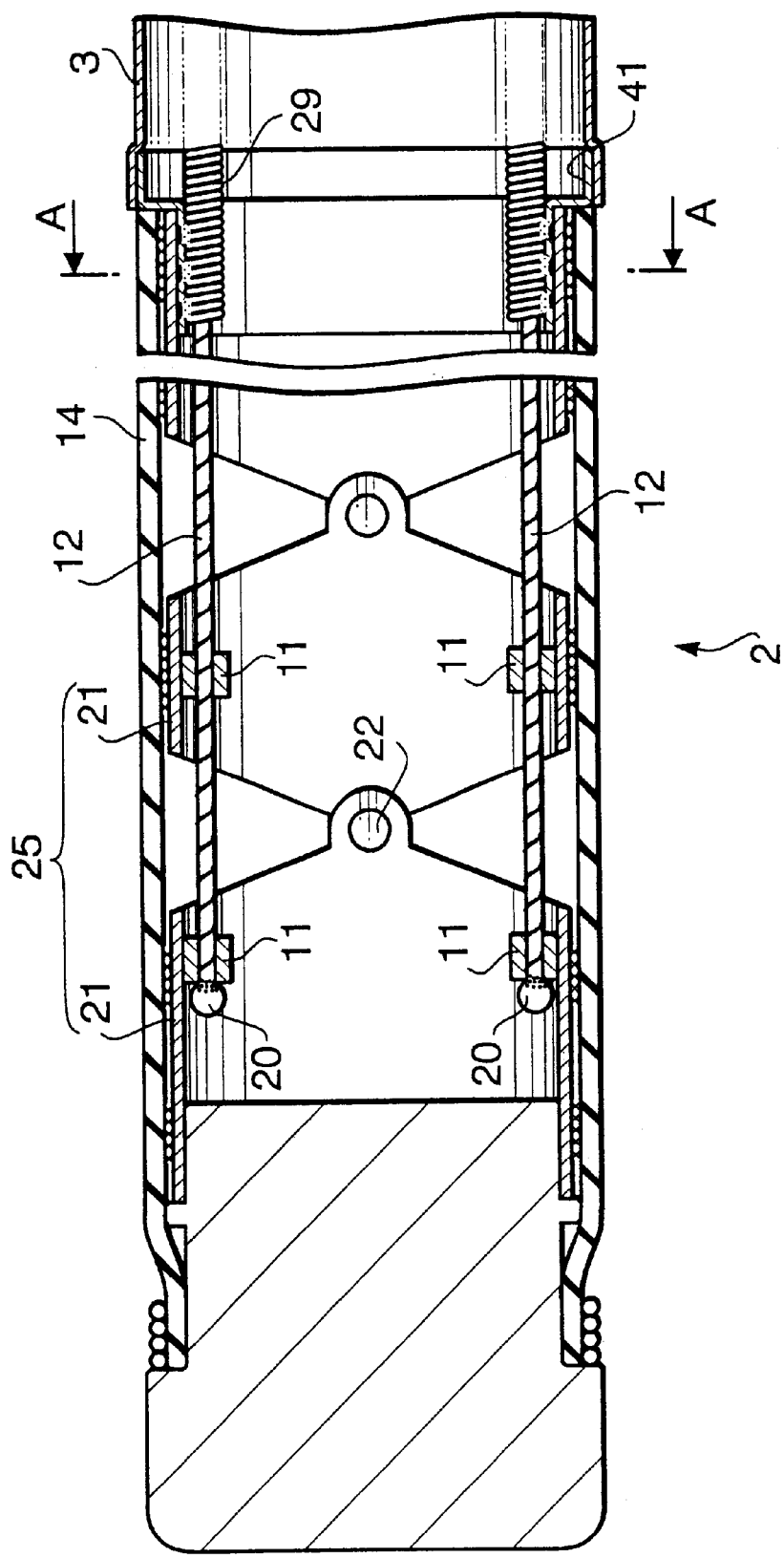
Figure 16:
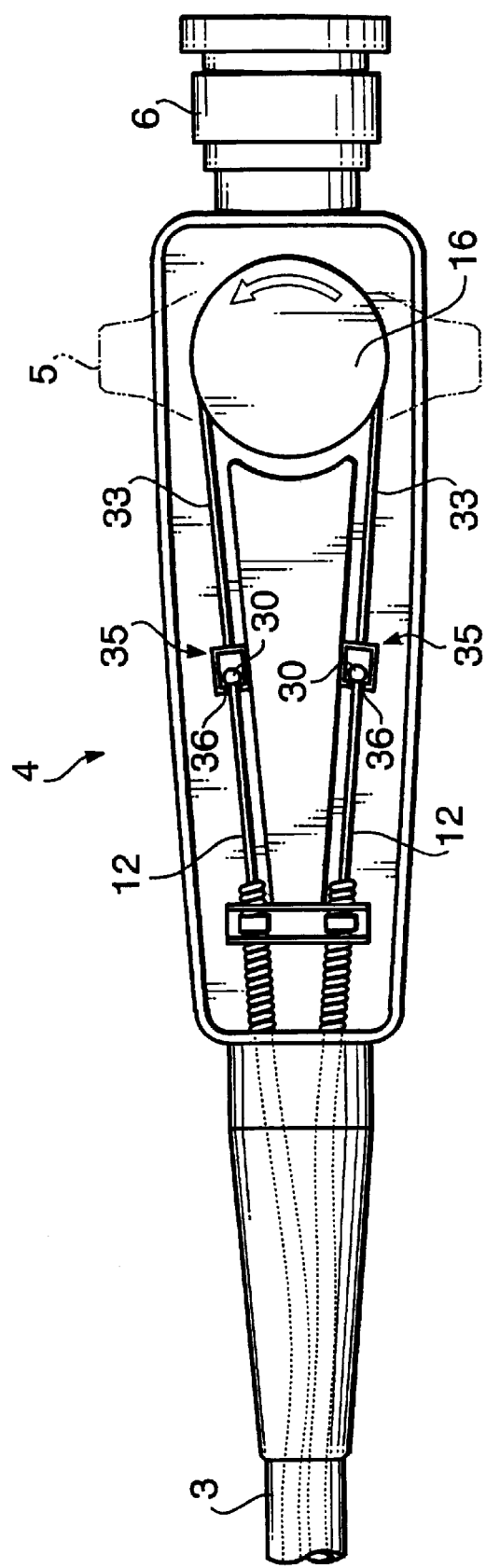
Figure 17:
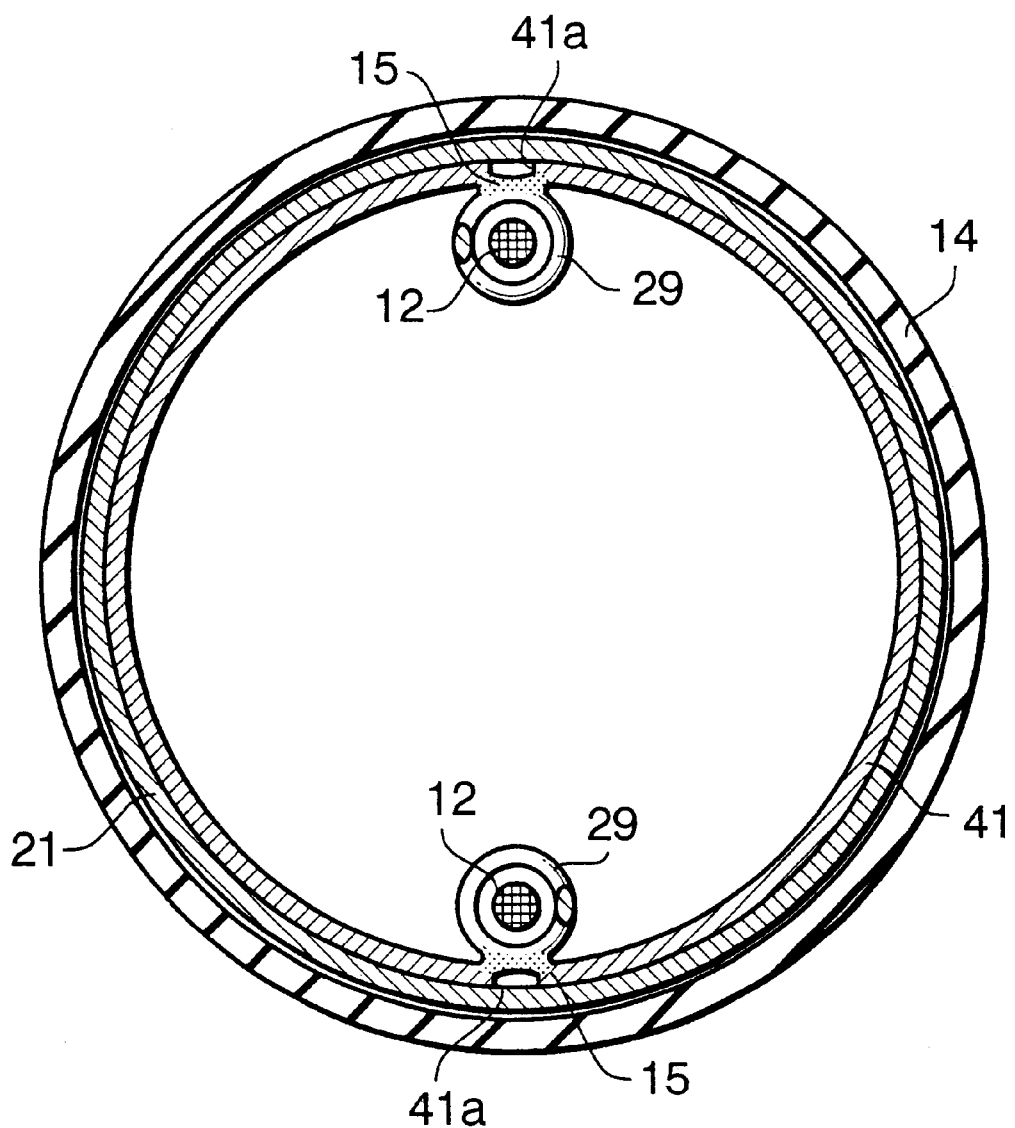
Figure 18:
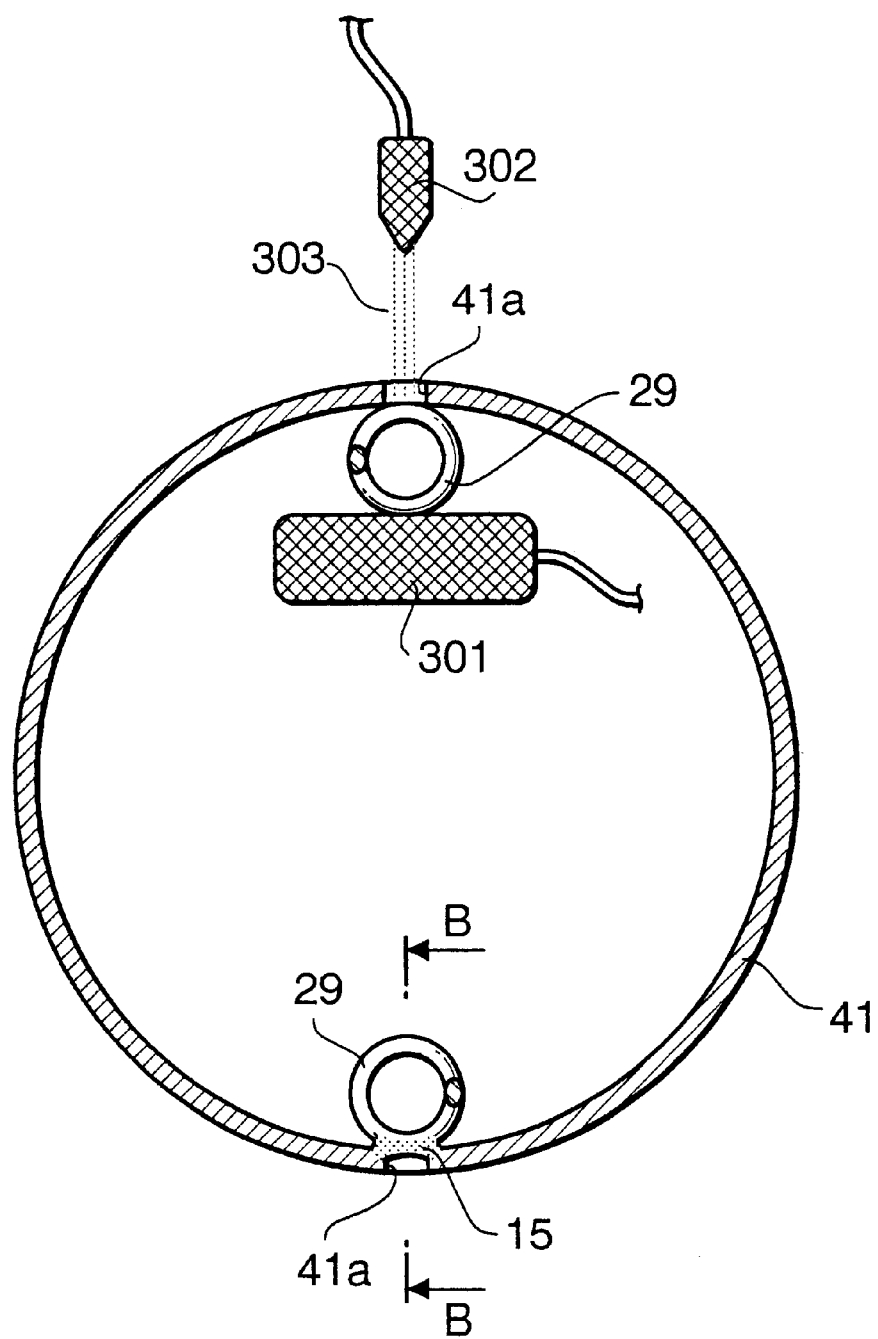
Figure 19:
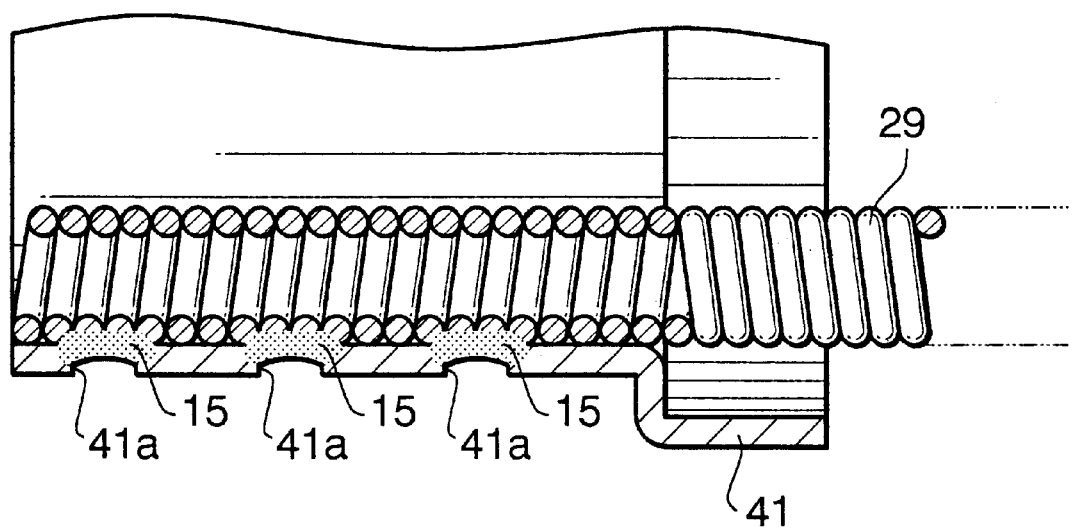
Figure 20:
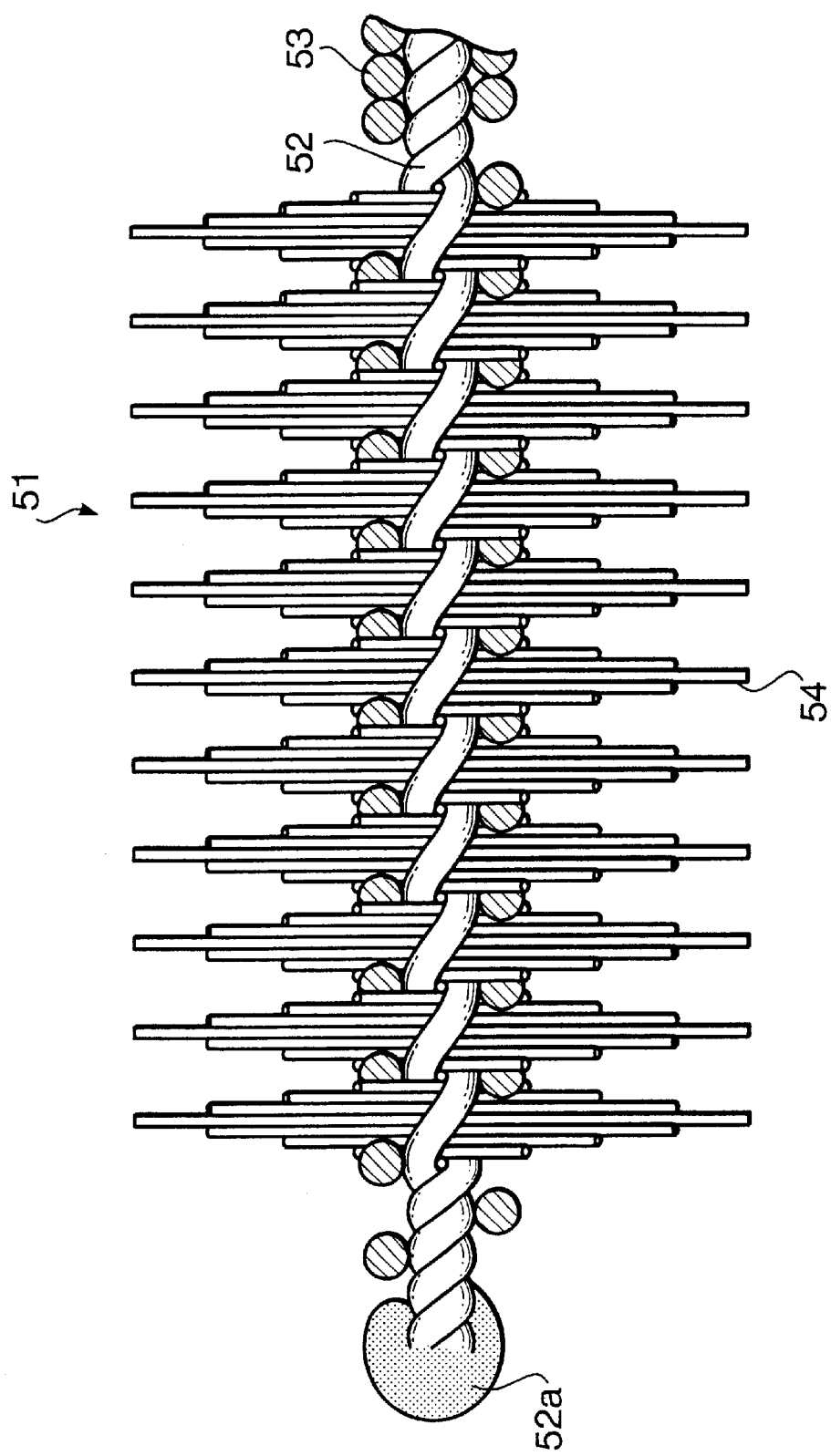
Figure 21:
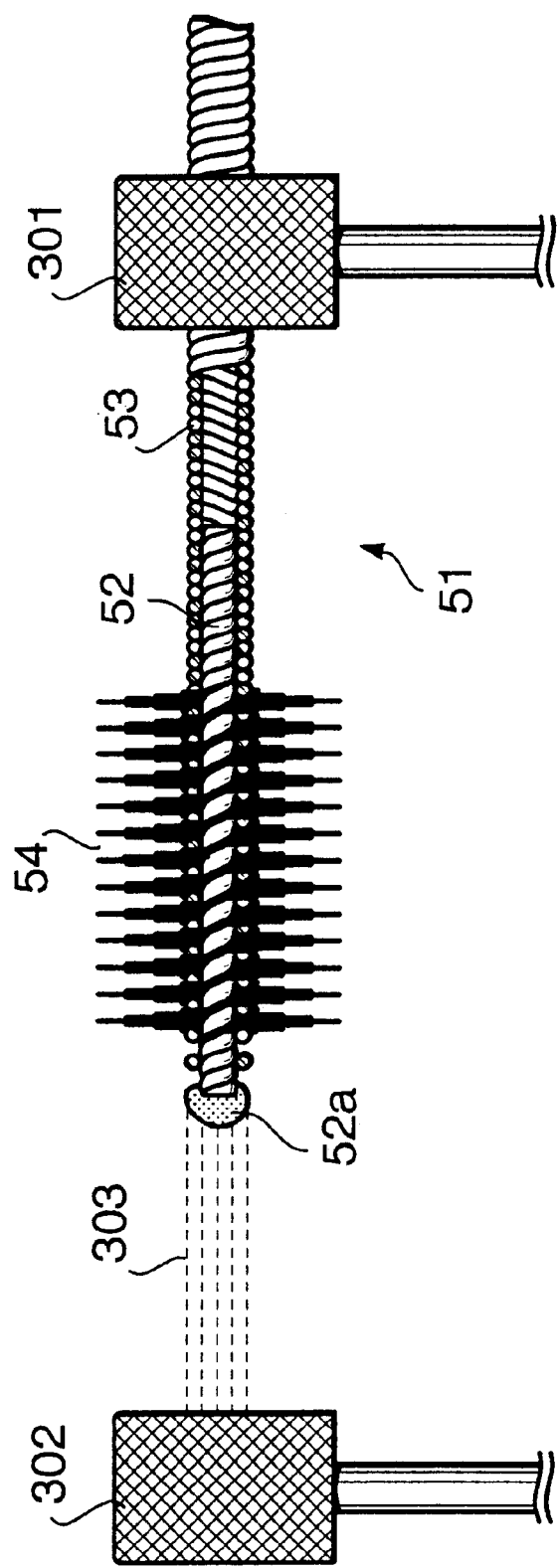
Figure 22:
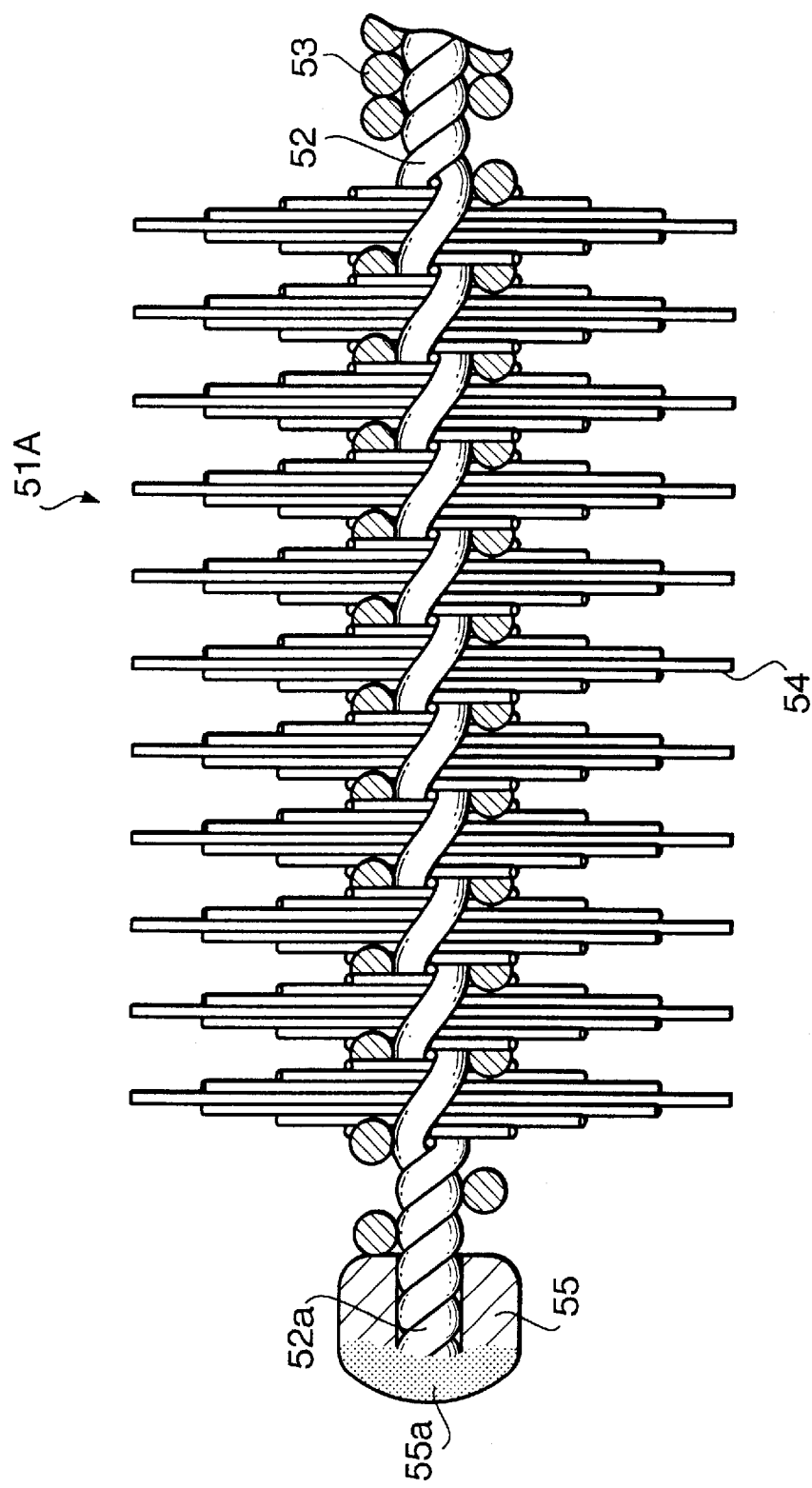
Figure 23:
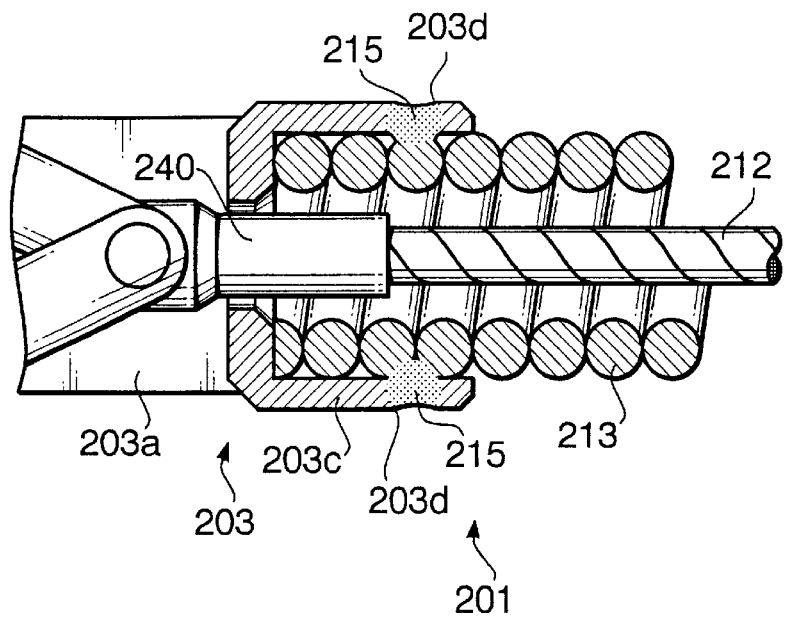
Figure 24:
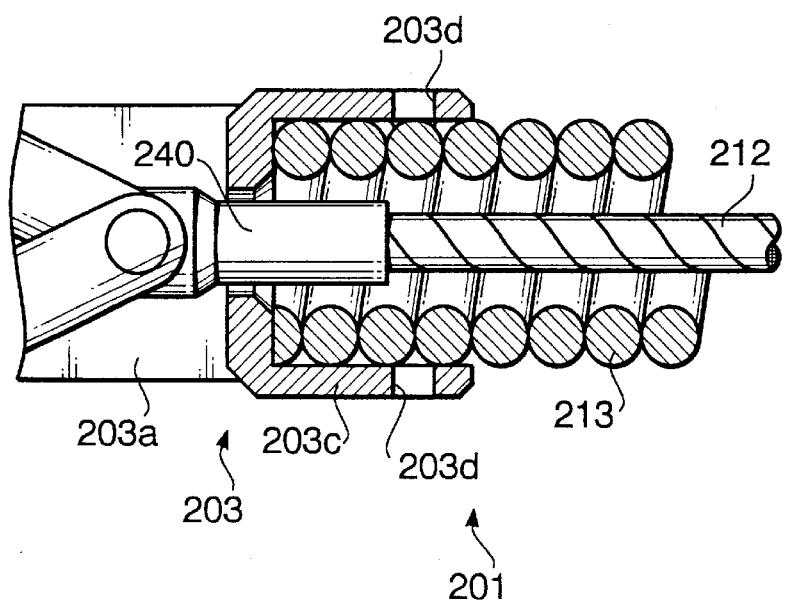
Figure 25:
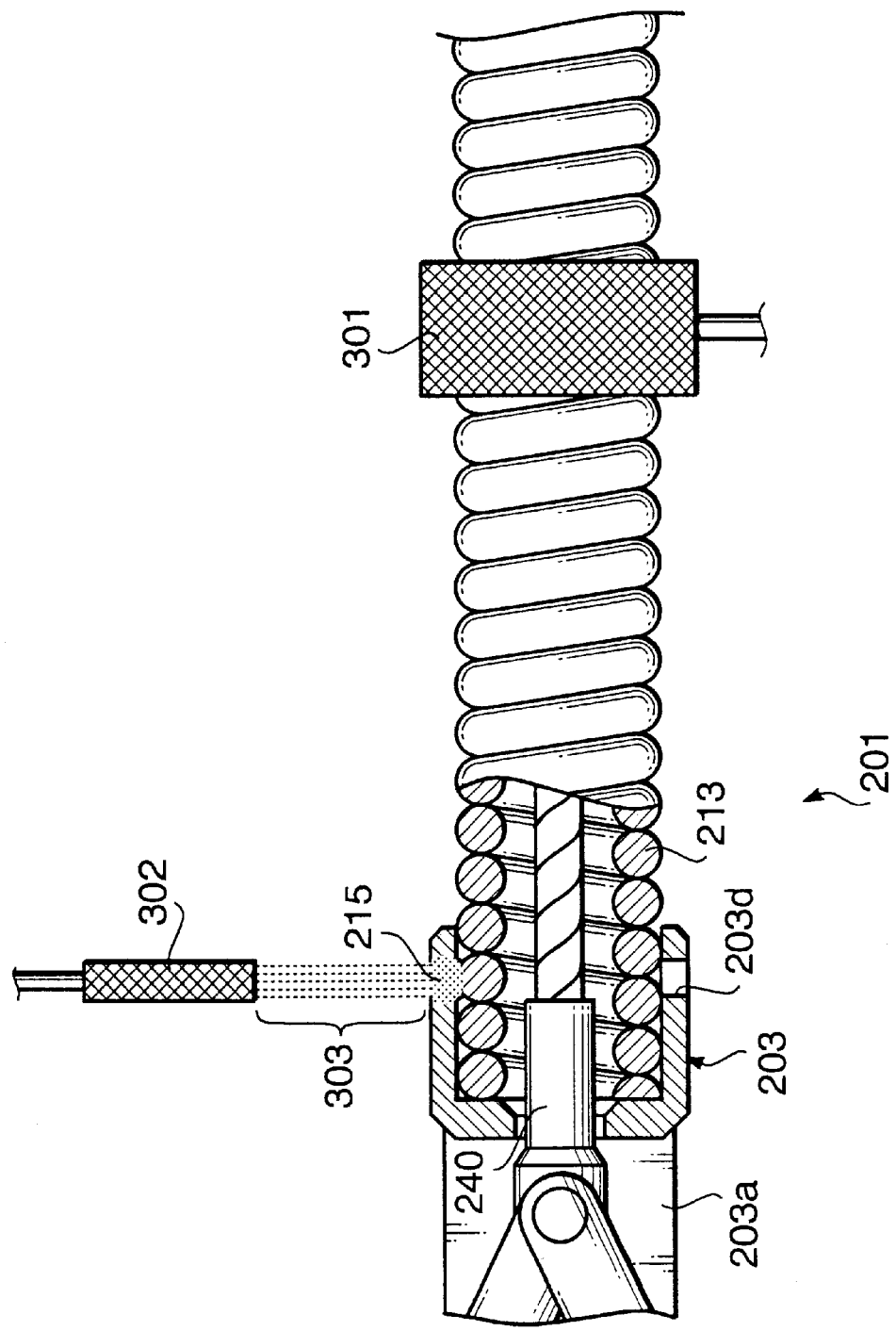
Figure 26:
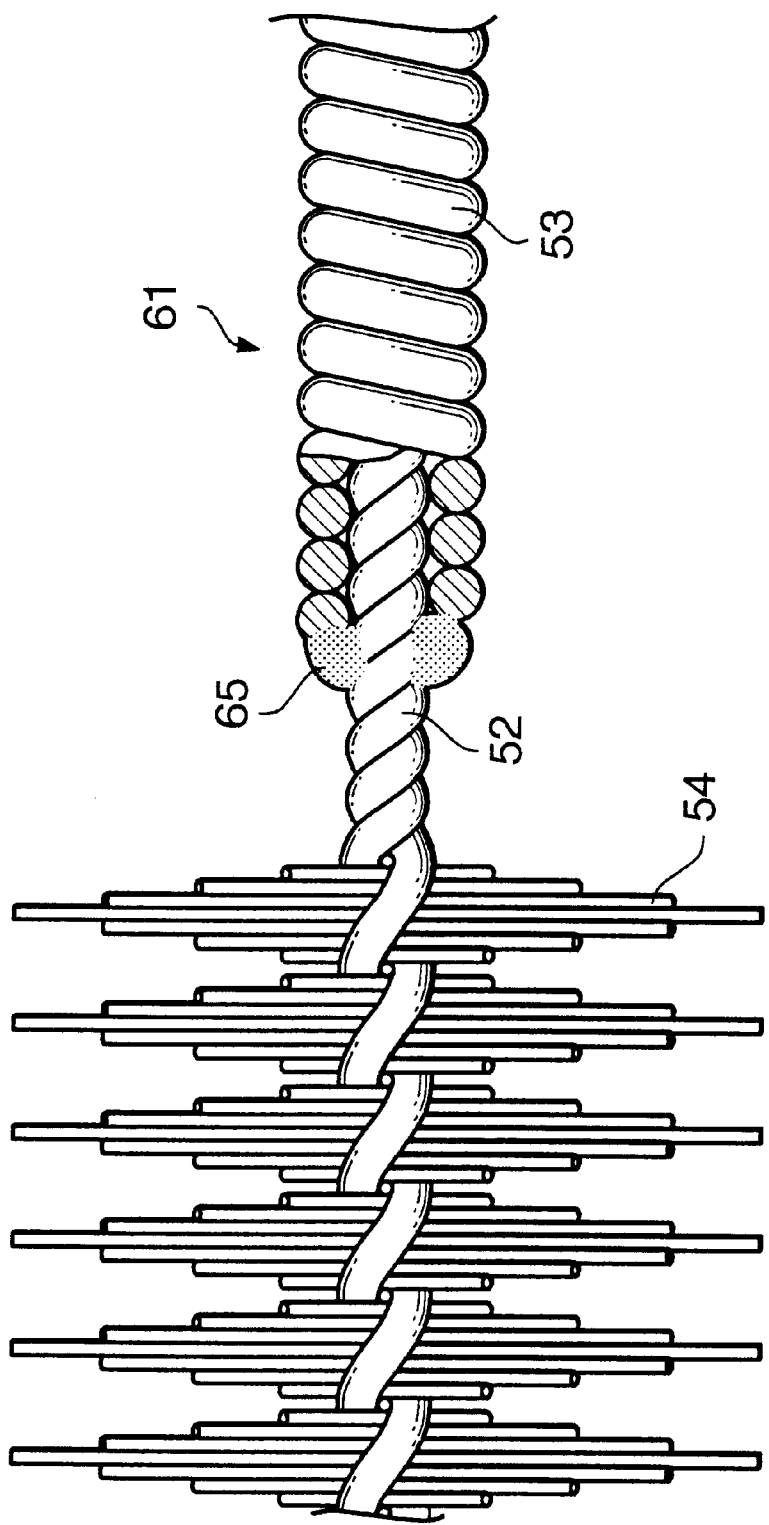
Figure 27:
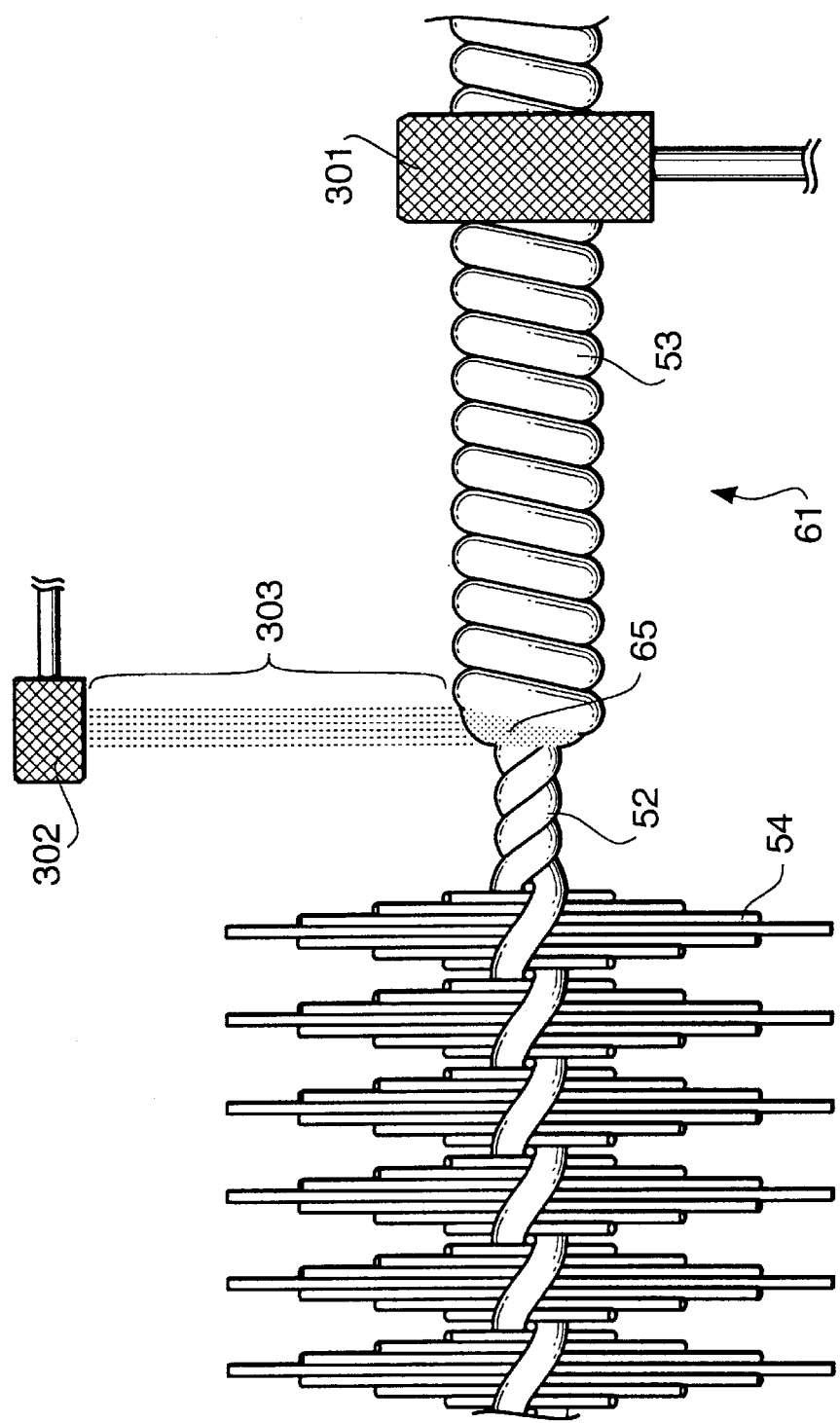
Figure 28:
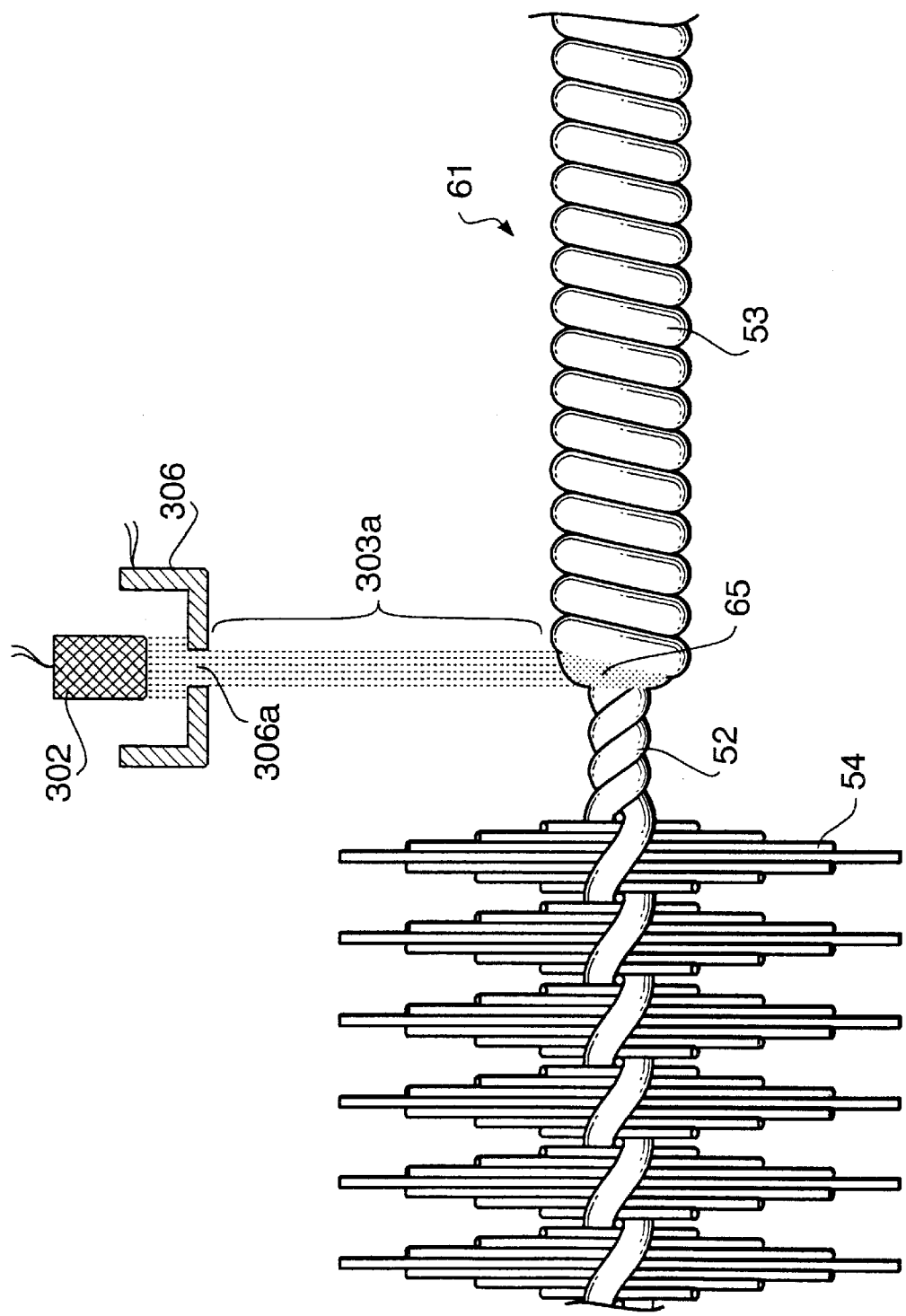
Figure 29:
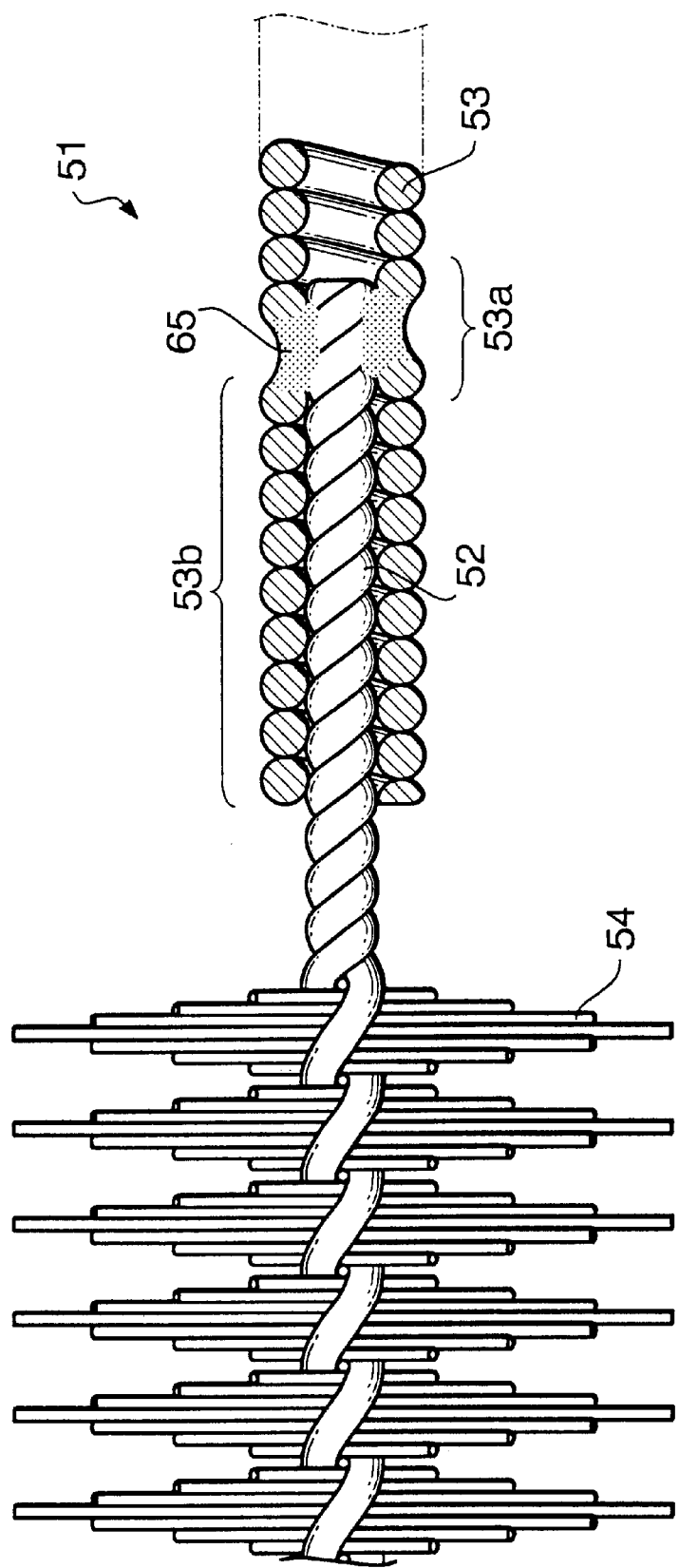
Figure 30:
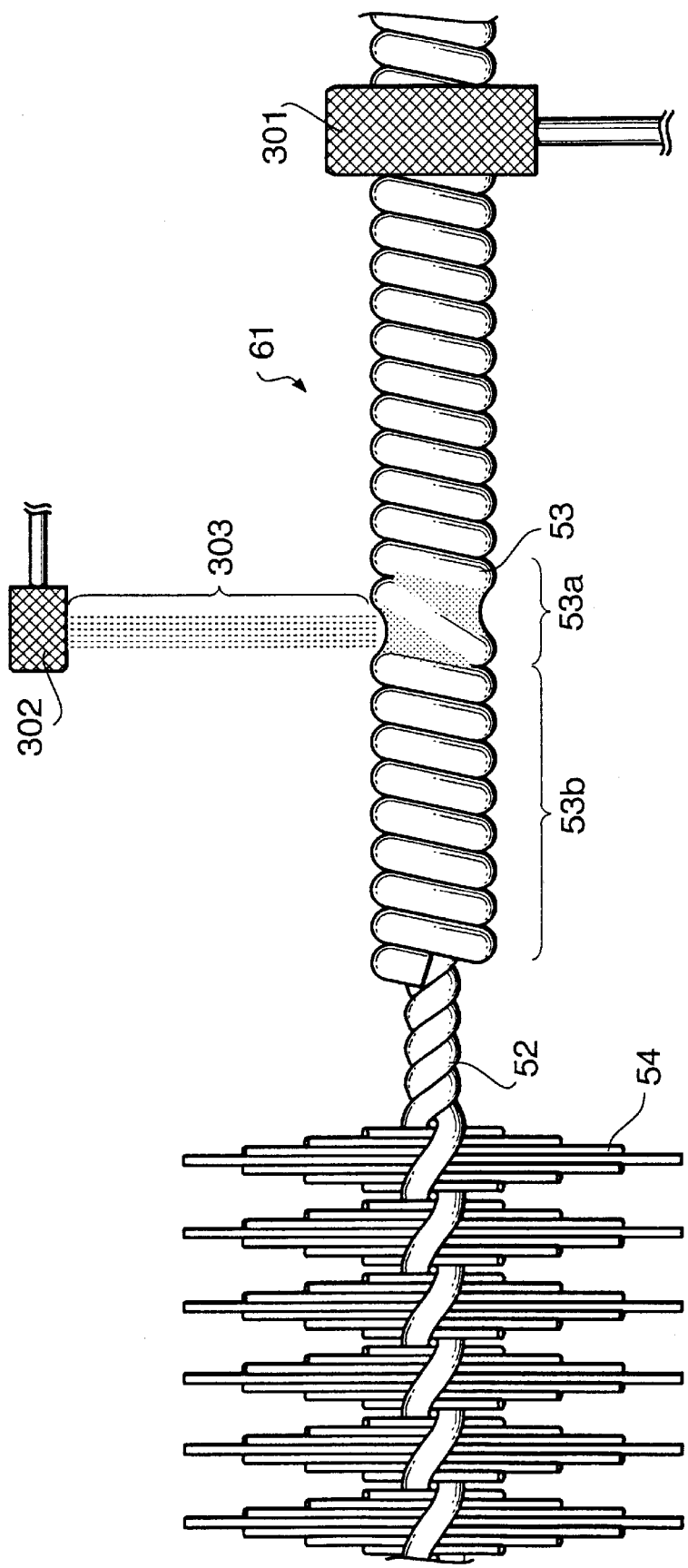
Figure 31:
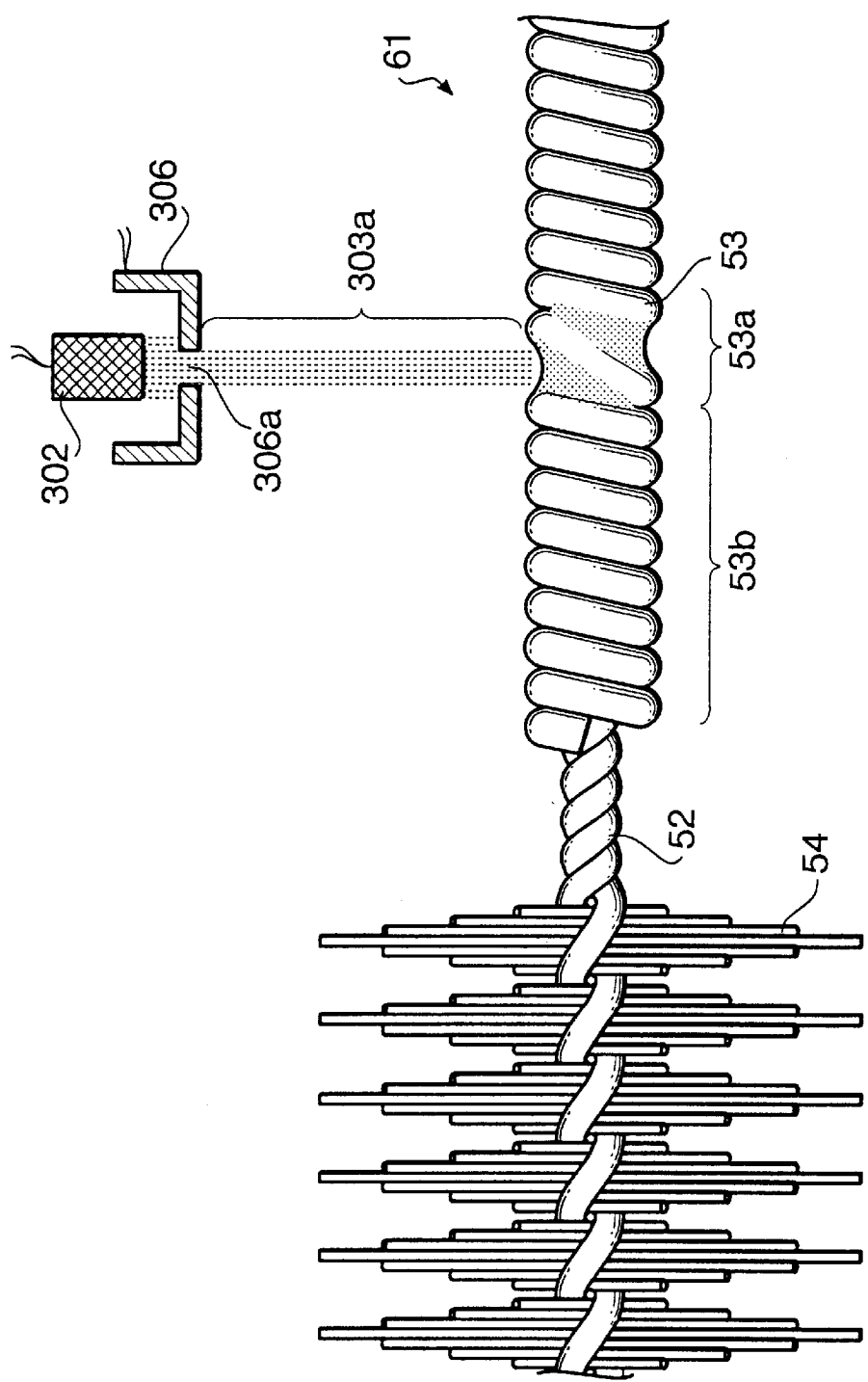
Figure 32:
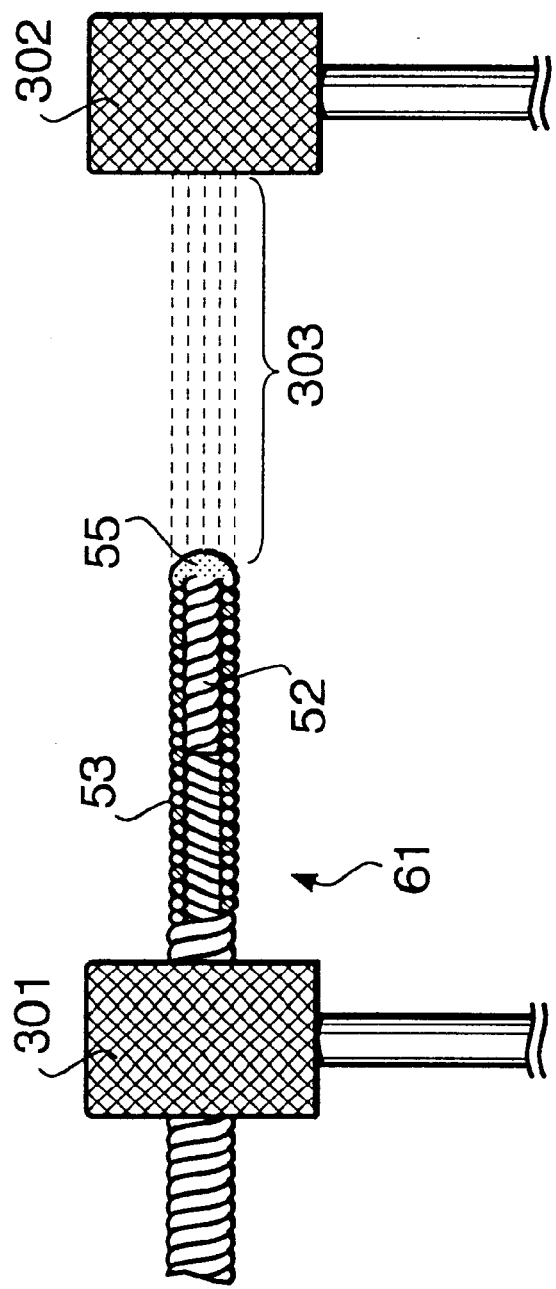
Figure 33:
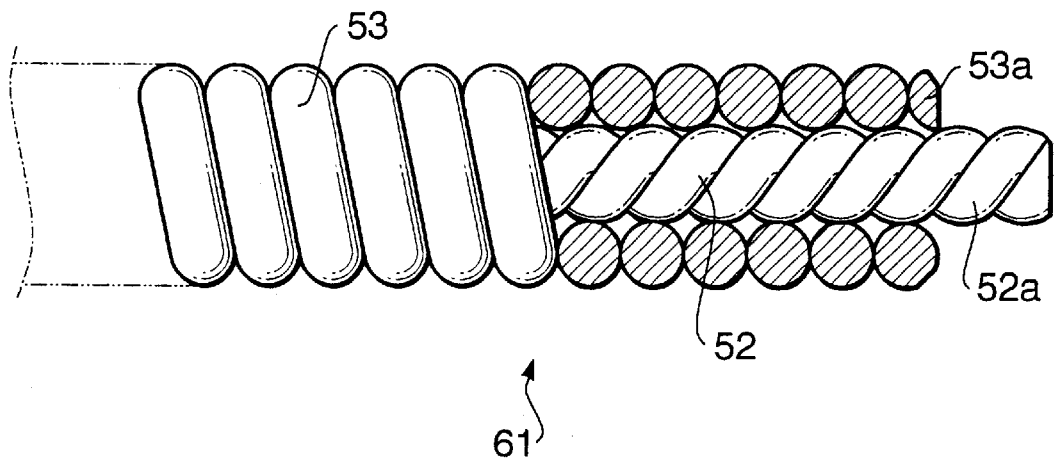
Figure 34:
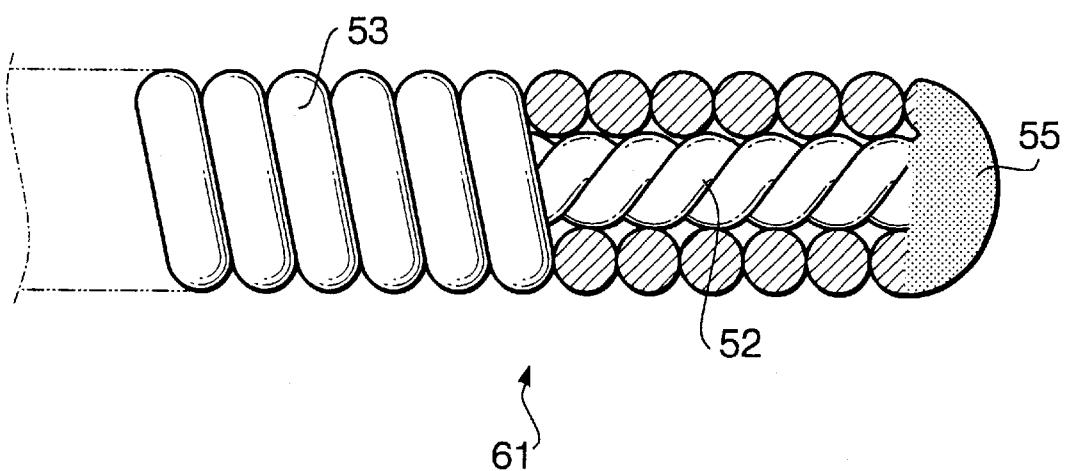

FIG. 5 schematically shows connection portion according to a second embodiment of the invention;

FIG. 6 shows how the first and second coils are connected;

FIG. 7 shows a manufacturing method of a connection portion according to a third embodiment;

FIG. 8 shows an endoscope through which a biopsy forceps according to the fourth embodiment is inserted;

FIG. 9 shows the biopsy forceps;

FIG. 10 shows a cross section of the bendable unit of the endoscope;

FIG. 11 is a cross-sectional view of the operation unit;

FIG. 12 is an enlarged cross-sectional view of the operation unit;

FIG. 13 is a cross sectional view of a part of the operation wire;

FIG. 14 shows a method of generating the arc column;

FIG. 15 shows an enlarged cross-sectional view of the bendable unit of the endoscope shown in FIG. 1 or FIG. 8;

FIG. 16 is a cross-sectional view of the operation unit;

FIG. 17 is a cross section taken along line A—A of FIG. 15;

FIG. 18 shows when the connection portions are formed to connect the guide coils to the metal connector;

FIG. 19 shows a cross-sectional view taken along line B—B of FIG. 18;

FIG. 20 shows a side view of a cleaning brush for cleaning the instrument channel of the endoscope, according to a sixth embodiment;

FIG. 21 shows the process for forming the spherical portion at the tip of the operation wire;

FIG. 22 shows a brush instrument according to a seventh embodiment of the invention;

FIGS. 23 and 24 show cross-sectional views of a part of the biopsy forceps shown in FIG. 2, according to an eighth embodiment;

FIG. 25 shows how the supporting member and the coil is connected;

FIG. 26 shows a side view of a cleaning brush according to a ninth embodiment;

FIG. 27 shows how the cover coil is connected to the operation wire;

FIG. 28 shows another method of exposing the tip of the cover coil to the arc column, according to a tenth embodiment;

FIG. 29 is a partially cross-sectional side view of a part of a cleaning brush instrument according to an eleventh embodiment;

FIG. 30 shows a procedure for forming the connection portion;

FIG. 31 shows another method of exposing the interstice portion to the arc column, according to a twelfth embodiment;

FIG. 32 shows a tip end portion of a cytological brush instrument according to a thirteenth embodiment;

FIGS. 33 and 34 show how the coil and the wire are connected; and

Figure 35:
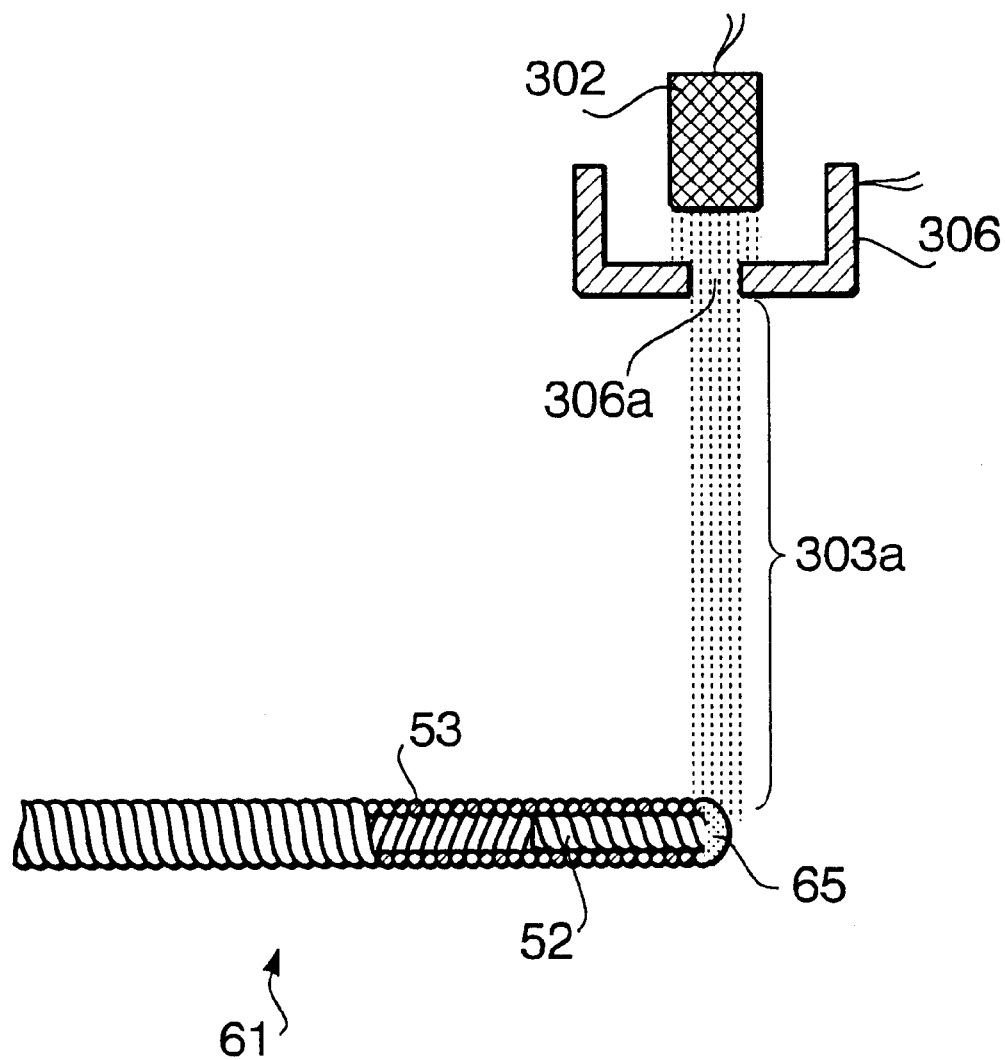

FIG. 35 shows another method of exposing the tip of the wire to the arc column, according to a fourteenth embodiment.

DETAILED DESCRIPTION OF THE EMBODIMENTS

Hereinafter, instruments for endoscopes according to embodiments of the invention will be described in detail, with reference to the accompanying drawings.

First Embodiment

FIG. 1 shows an endoscope 1, to which a biopsy forceps is connected, which is manufactured according to a first embodiment.

The endoscope 1 has a flexible insertion tube 3. A bendable unit 2 of the insertion tube 3 is to be inserted in a human cavity. At the distal end portion of the bendable unit 2, an objective optical system is provided. An object image entering from the objective lens is observed through an eyepiece unit 6. By rotating an operation knob 5 provided on an operation unit 4, the bendable unit 2 can be bent arbitrarily.

The endoscope is formed with a instrument insertion opening 7. A biopsy forceps 201, or another treatment instrument can be inserted, from the instrument insertion opening 7, through an instrument insertion channel 10. When the biopsy forceps 201 is inserted, a first forceps cup 205a and a second forceps cup 205b protrude from the distal end of the endoscope 1. By operating an operation handle 225 provided to the proximal end portion of the biopsy forceps 201 to move in a direction along the axis thereof, the first and second forceps cups 205a and 205b can be opened and closed.

FIG. 2 shows a cross section of the distal end portion and the proximal end portion of the biopsy forceps 201. The first and second forceps cups 205a and 205b have plate-shaped arms 206a and 206b which are integrally formed with the cups 205a and 205b. The arms 206a and 206b are formed with a hole 211, and at which, the arms 206a and 206b are rotatably supported by a pin 204. With this structure, by rotatably moving the arms 206a and 206b, the cups 205a and 205b can be opened or closed.

The pin 204 is secured on a supporting member 203. The portion of the supporting member 203 where the arms 206a and 206b move are formed as a slit portion 203a.

Each of the arms 206a and 206b is formed with a link engaging hole 221, which engages with a link shaft 214. Each link shaft 214 further engages with a link hole 222 formed on a link plate 207a or 207b. Thus, the link plates 207a and 207b are rotatable about the link shafts 214, respectively.

Further, as shown in FIG. 2, each of the link plates 207a and 207b is formed with an engaging hole 231, through which an supporting pin 234 is rotatably inserted. The supporting pin 234 is secured onto a metal connector 240. Furthermore, the metal connector 240 is connected with the distal end of an operation wire 212. The proximal end portion of the operation wire 212 is connected to an operation slider 225. With this configuration, by moving (sliding) the operation slider 225, the operation wire 212 can be moved along its axis. The metal connector 240 is slidably fitted in an through hole 203b defined on the supporting member 203. Thus, as the operation wire 212 moves in the axial direction thereof, the metal connector 240 moves such that a distance between the pins 204 and 234 varies. That is, if the metal connector 240 is moved in the direction where the pin 234 approaches the pin 204, the biopsy forceps cups 204a and 204b open, while if the metal connector 240 is moved in the direction where the pin 234 is away from the pin 204, the biopsy forceps cups 204a and 204b close.

In order to prevent the operation wire 212 from bending too sharply, the operation wire 212 is covered with a coil 213, which elastically protect the operation wire 212. Further, to allow smooth slidable movement of the operation wire 212 inside the first coil 213, the distal end of the first coil 213 is connected with the supporting member 203. The proximal end side portion of the operation wire 212 is covered with a second coil 223, which has a greater wire diameter than the first coil 213. It should be noted that the distal end portion of the wire 212 should follow the curve formed by the bendable unit 2, and therefore, the first coil 213 is formed by a relatively thin wire so that the first coil 213 is sufficiently flexible. On the contrary, a portion of the second coil 223 located at the flexible tube 3 is formed by a relatively thick wire so that the second coil 223 is not bent easily. Using a connection pipe 233, the first coil 213 and the second coil 223 are connected so that the wire 212 is covered with the first coil 212 or the second coil 223 without a non-covered portion along its length. The connection portion 101 will be described in detail hereinafter.

Figure 3:
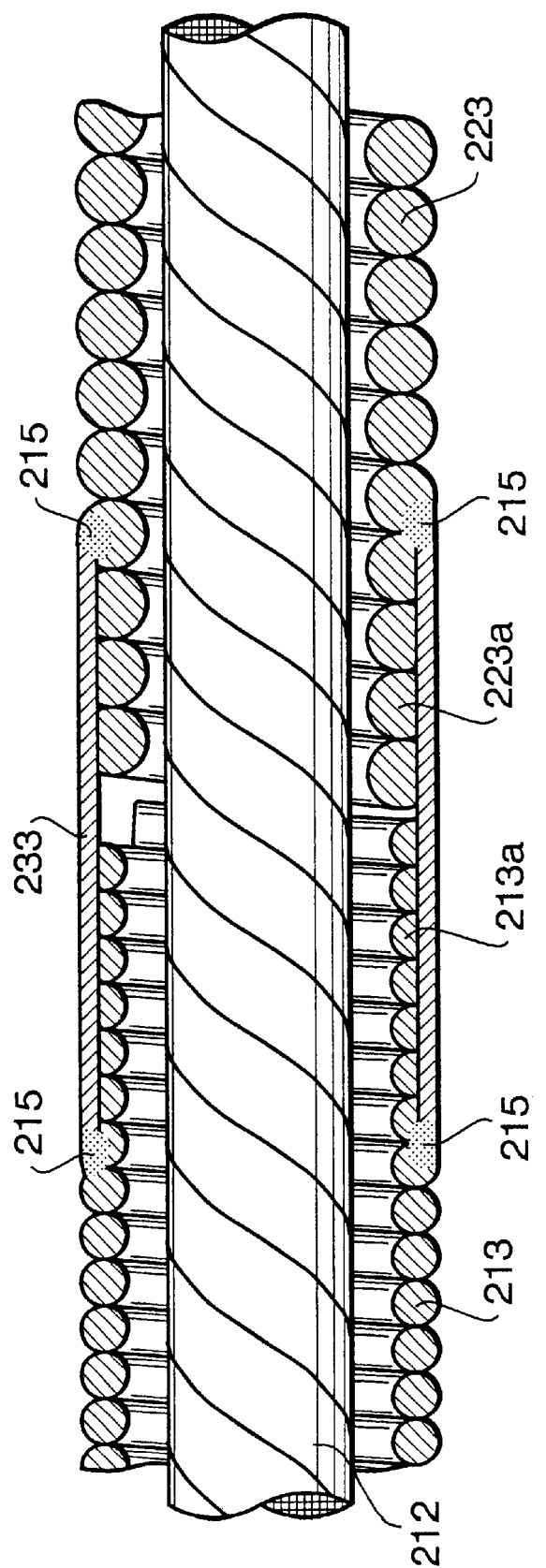
FIG. 3 shows an enlarged cross-sectional view of the connection portion.

FIG. 3 shows an enlarged cross-sectional view of the connection portion 101.

The proximal end portion of the first coil 213 is formed to be an insertion end 213a, and the distal end portion of the second coil 223 is formed to be an insertion end 223a. Each of the insertion portion 213a and 223a are formed such that the outer diameter thereof is less than but substantially equal to the inner diameter of the connection pipe 233. Therefore, the insertion end 213a of the first coil 213 and the insertion end 223a of the second coil 223 are smoothly inserted in the connection pipe 233. It should be noted that the outer diameter of the connection pipe 233 is substantially the same as the outer diameter of the first coil 213 and the second coil 223, and therefore, the connection portion 101 can be inserted in the treatment instrument channel 10 of the endoscope 1 smoothly, without being caught thereby.

According to the first embodiment, the end portions of the connection pipe 233 and the first and second coils 213 and 223 are connected with an arc welding method. That is, predetermined portions of each end of the connection pipe 233 and the outer surface of the first coil 213 or the second coil 223 are exposed to arc so that the exposed portions are melted and connected. The melted and connected portions are indicated as connected portions 215 in FIG. 3. It should be noted that the connected portions 215 are distributed on four through six circumferential positions.

Figure 4:
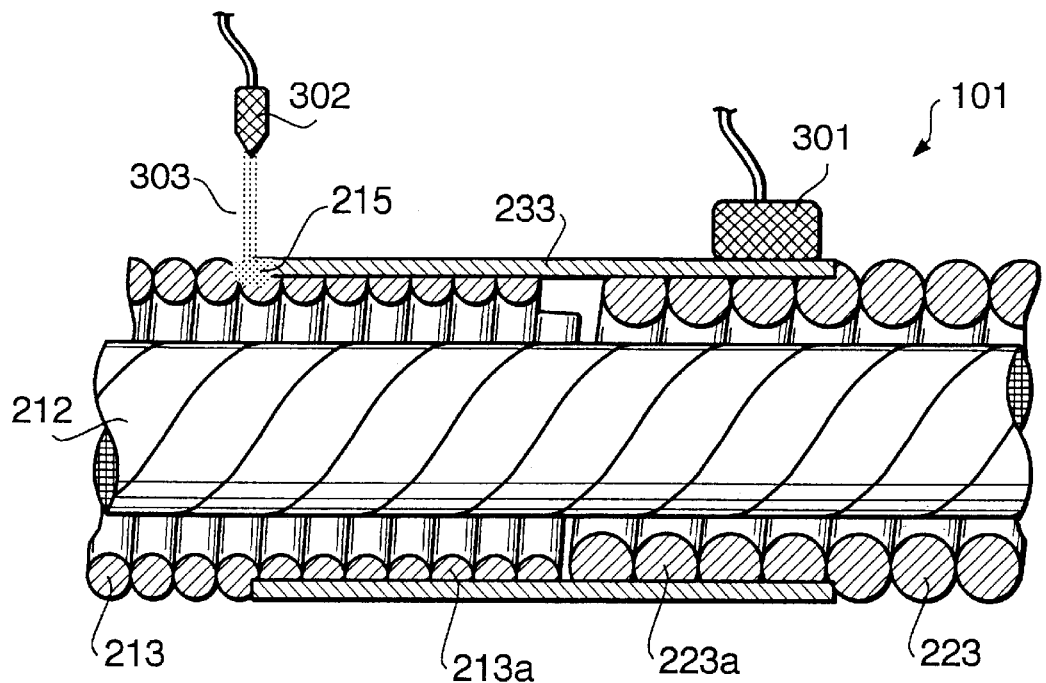
FIG. 4 shows a condition where the arc welding is performed.

FIG. 4 shows a condition where the arc welding is performed. A first electrode 301 is placed on the connection pipe 233, and a second electrode 302 is located in the vicinity of a portion where the end of the connection pipe 233 and the first coil 213 is connected. For preventing oxidization of the connected portion, Argon gas is filled around the second electrode 302.

By applying a predetermined electrical power between the first electrode 301 and the second electrode 302, an arc column 303 is generated between the second electrode 302 and a portion of the connection pipe 233 closer to the second electrode 302. Since the temperature of the arc column is 5000K or more, the portion of the connection pipe 233 and a portion of the outer surface of the first coil 213 adjacent thereto are melted. Thereafter, by stopping the power supply between the first and second electrodes 301 and 302, the arc column 303 is disappeared and the melted metal is cooled to the solidifying point. As a result, the first coil 213 and the connection pipe 233 are connected strongly. The other portions are melted and connected in a similar manner.

Second Embodiment

FIG. 5 schematically shows connection portion 101A according to a second embodiment of the invention. The structure of the biopsy forceps other than the connection portion 101A is similar to the structure of the first embodiment, and therefore, description of the endoscope other than the connection portion 101A will not be repeated.

According to the second embodiment, an operation wire 212 at the distal end portion is covered with a first coil 213 formed of a thin wire, and the portion inserted in the flexible tube 3 is covered with a second coil 223 formed of a thick wire. With this configuration, the first coil 213 functions as a flexible coil, while the second coil 223 serves as a rigid coil. The proximal end of the first coil 213 and the distal end of the second coil 223 contact with each other.

In the second embodiment, the portion where the proximal end of the first coil 213 and the distal end of the second coil 223 contact is exposed to an arc column so that the portion is melt and connected. Thus, as shown in FIG. 5, connection portions 215 are formed at the portions where the proximal end of the first coil 213 and the distal end of the second coil 223 contact with each other. In FIG. 5, four portions are indicated as the connection portions 215. However, in order to provide sufficient connection forth, the number of the connection portions 215 may be increased to, for example, six.

FIG. 6 shows how the first and second coils 213 and 223 are connected. As shown in FIG. 6, a first electrode 301 contacts a portion where the proximal end of the first coil 213 and the distal end of the second coil 223 contact. A second electrode 302 is located in the vicinity of a position where the proximal end of the first coil 213 and the distal end of the second coil 223 contact. The first electrode 301 and the second electrode 302 are arranged such that the operation wire 212 is located therebetween. Further to this configuration, in order to avoid oxidization of the connected portions, an area surrounding the second electrode 302 is filled with Argon gas.

By applying a predetermined electrical power between the first electrode 301 and the second electrode 302, an arc column 303 is generated between the second electrode 302 and a portion which is closer to the second electrode 302 and where the proximal end of the first coil 213 and the distal end of the second coil 223 contact. Since the temperature of the arc column is 5000 K or more, the portion where the proximal end of the first coil 213 and the distal end of the second coil 223 contact is melted. Thereafter, by stopping the power supply between the first and second electrodes 301 and 302, the arc column 303 is disappeared and the melted metal is cooled to the solidifying point. As a result, the first coil 213 and the second coil 223 are connected strongly. The other connection portions 215 are melted and connected in a similar manner.

According to the second embodiment, the arc column 303 is generated on the outer surface of the first and second coils 213 and 223. Therefore, only the surface of the first and second coils 213 and 223 is heated. Accordingly, it is not necessary to grind the proximal end surface of the first coil 213 and the distal end surface of the second coil 223 as in the prior art, wherein a laser beam is used for melting the coils.

Third Embodiment

FIG. 7 shows a manufacturing method of a connection portion 101B according to a third embodiment. The third embodiment is similar to the first embodiment except that a plurality of through holes 233H are formed on the connection pipe 233. As shown in FIG. 7, a first electrode 301 is placed on the connection pipe 233, and a second electrode 302 is located above the through hole 233H. For preventing oxidization of the connected portion, Argon gas is filled around the second electrode 302.

By applying a predetermined electrical power between the first electrode 301 and the second electrode 302, an arc column 303 is generated between the second electrode 302 and the through hole 233H through which the surface of the first or second coil 213 or 223 is exposed. Since the temperature of the arc column is 5000K or more, the edge defining the through hole 233H and a portion of the outer surface of the first coil 213 exposed to outside through the through hole 233H are melted. Thereafter, by stopping the power supply between the first and second electrodes 301 and 302, the arc column 303 disappears and the melted metal is cooled to the solidifying point. As a result, the first coil 213 or the second coil 223 and the connection pipe 233 are connected strongly.

Fourth Embodiment

FIG. 8 shows an endoscope through which a biopsy forceps 100 according to the fourth embodiment is inserted. Similarly to the endoscope shown in FIG. 1, the biopsy forceps 100 is inserted from the instrument insertion opening 7 of the endoscope. A pair of forceps cups 105 protrude from the distal end of the bendable unit 2 of the endoscope 1.

FIG. 9 shows the biopsy forceps 100. To the forceps cups 105, an end of the operation wire 107 is connected, and upon movement of the wire 107 along its axis, the forceps cups 105 open and close.

In order to allow a smooth movement of the operation wire 107, it is inserted through a first guide coil 104. The inner surface of the first guide coil 104 is formed to be smoothly slidable with respect to the operation wire 107. Thus, the operation wire 107 is slidable inside the guide coil 104 without snagging. Further, since the operation wire 107 is covered with the first guide coil 104, the wire 107 is prevented from being hooked to fingers of an operator or the like.

The other end of the operation wire 107 is connected to an operation slider 108 of an operation mechanism 103. The operation slider 108 is slidably supported by a cylindrical guide 106, in which the proximal end portion of the first guide coil 104 is fitted. With this structure, by sliding the operation slider 108 along the cylindrical guide 106, the operation wire 107 can be moved along its axis to operate the forceps cups 105.

Most of the endoscopes are provided with a bendable unit which is remotely driven to bend using an endoscope operating wire.

FIG. 10 shows a cross section of the bendable unit 2 of the endoscope 1. The bendable unit 2 has a plurality of ring members 21 which are rotatably connected by pins 22. The above structure of the bendable unit 2 is inserted. In each ring member 21, a pair of wire guides 11 are provided. A pair of operating wires 12 are inserted through the plurality of ring members 21, and supported by the wire guides 11. The pair of wire guides 11 of each ring member 21 are located at opposite positions with respect to the central axis thereof.

FIG. 11 is a cross-sectional view of the operation unit 4. As shown in FIG. 11, the proximal ends of the operating wires 12 and both ends of a wire 33 are connected through a sag/tension removing devices 35 and 35. The central portion of the wire 33 is wound around a pulley 16 which is coaxial with respect to the operation knob 5.

One of the operating wires 12 is inserted in one of the pair of wire guides 11, and the other of the operating wires 12 is inserted in the other of the pair of wire guides 11. Then, the tips of the operating wires 12 are processed to have a larger diameter than the inner diameter of the cylindrical portion of the wired guides 11. With this structure, the tips of the pair of operating wires 12 are engaged with the wire guides 11 of the distal end side ring member 21.

With this structure, when the operation knob 5 is rotated and the pulley 16 rotates, one end of the wire 33 is pushed toward the bendable unit side of the endoscope 1, and the other end of the wire 33 is pulled toward the proximal end side of the operation unit 4. Thus, the two wires 12 are moved in the opposite directions, thereby the bendable unit 2 being bent.

In order to allow a smooth movement of the wires 12 in the flexible tube 3 of the endoscope 1, each of the wires 12 is inserted through a second guide coil 13, as shown in FIG. 12. The inner surface of the guide coils 13 are made smooth so that the wire 12 slides therein. With this configuration, the operating wires 12 are slidable in the second guide coils 13 without sags.

As shown in FIG. 9, between the first guide coil 104 and the guide 106, a first coil 101 is provided. The first coil 101 prevents concentration of the force applied to the first guide coil 104 at the end of the support 106. That is, if the first coil 101 is not provided, the first guide coil 104 may be bent due to the force applied thereto at the position where the first guide coil 104 contacts the end of the support 106. Since the first coil 101 is provided, it is ensured that the first guide coil 104 will not be bent, and therefore, the operation wire 107 can be smoothly moved.

FIG. 12 is an enlarged cross-sectional view of the operation unit 4. As shown in FIG. 12, the diameter of the operation unit 4 is gradually reduced toward the flexible tube 3. In order to prevent the second guide coils 13 from being damaged as they contact corner portions 4a inside the operation unit 4, the second guide coils 13 are inserted in second coils 15, respectively.

FIG. 13 is a cross sectional view of a part of the operation wire 107, the first guide coil 104 and the first coil 101. As indicated in FIG. 13, the first guide coil 104 and the first coil 101 are connected at a plurality of portions, the connection portions being indicated by reference numerals 115. As shown in FIG. 13, each of the connection portions 115 is formed such that a part of the first coil 101 and the corresponding part of the first guide coil 104 are melted. It should be noted that the outer surface of the first guide coil 104 is melted, but the inner surface of the first guide coil 104 is not melted. Therefore, even though the first coil 101 is firmly connected with the outer surface of the first guide coil 104, the inner surface of the first guide coil 104 is not connected to the operation wire 107.

In the embodiment, the first cover coil 101 and the first guide coil 104 are melted by generating an arc column. FIG. 14 shows a method of generating the arc column. As shown in FIG. 14, a first electrode 301 is secured to the first cover coil 101, and a second electrode 302 is arranged in the vicinity of the first cover coil 101. Further, in order to prevent oxidization of the connection portion, an area surrounding the second electrode 302 is filled with Argon gas.

By applying a predetermined power between the first and second electrodes 301 and 302, an arc column 303 is generated between the second electrode 302 and the first cover coil 101 at a portion adjacent to the second electrode 302. Since the temperature of the arc column is 5000K or more, the portion of the first cover coil 101 exposed to the arc column 303 and the corresponding portion of the first guide coil 104 are melt. Then, the power supply to the first and second electrodes 301 and 302 are terminated, the arc column disappears, and the melted metal is cooled down to the solidifying point. As a result, the first cover coil 101 and the first guide coil 104 are firmly connected as shown in FIG. 13.

It should be noted that by adjusting a period of time during which the predetermined power is supplied to the first and second electrodes 301 and 302, the temperature is controlled such that the outer surface of the first guide coil 104 is melted but the inner surface of the first guide coil 104 is not melted.

Although not shown in drawings, the second guide coil 13 covering the operating wire 12 and the second cover coil 15 can be connected in a similar manner.

Fifth Embodiment

FIG. 15 shows an enlarged cross-sectional view of the bendable unit 2 of the endoscope 1 shown in FIG. 1 or FIG. 8, according to a fifth embodiment of the invention. The bendable unit 2 is provided with a bending assembly 25, which includes a plurality of ring members 21 which are rotatably connected with pins 22. The bending assembly 25 is covered with a rubber tube 14. The ring member 21 is formed as a metal tube, end portions thereof being cut to be wedge-shaped. Each of the ring members 21 is provided with a pair of wire guides 11 on the inner surface thereof. In each ring member 21, the wire guides 11 are provided on substantially the same plane, which is perpendicular to the central axis of the ring member 21, and the wire guides 11 are located at opposite positions with respect to the central axis. Further, when all the ring members 21 are aligned along a straight line, the pair of wire guides are also aligned along straight lines, respectively. Through each wire guide 11, the operation wire 12 is inserted, and the distal end side of the operation wire 12 is formed to have a spherical shape 20 so that the end side of the wire 12 is not pulled out of the wire guide 11 of the distal end side ring member 21. It should be noted that the wire 12 may be a single wire or twisted wire.

Portions of the operating wires 12 inserted in the flexible tube 3 are covered with guide coils 29 for elastically protect the wires 12, respectively. Both ends of each guide coil 29 are fixed with respect to the flexible tube 3 so that the guide coil 29 does not move in the axial direction inside the flexible tube 3 when the operation wire 12 is moved.

The bendable unit 2 and the flexible tube 3 are connected using a metal connector 41, which is a cylindrical metal member. Further, the bendable unit sides of the guide coils 29 are secured on the inner surface of the metal connector 41.

FIG. 16 is a cross-sectional view of the operation unit 4, which is similar to the unit shown in Fig 11. As shown in FIG. 16, the proximal ends of the operating wires 12 and both ends of a wire 33 are connected through a sag/tension removing devices 35 and 35. The central portion of the wire 33 is wound around a pulley 16 which is coaxial with respect to the operation knob 5. Each of the sag/tension removing devices 35 is formed with a wire connection opening 36, through which each wire 12 is inserted. The inserted portion 30 of each wire 12 is formed to be spherical so that it is not pulled out of the connection opening 36.

With this structure, when the operation knob 5 is rotated and the pulley 16 rotates, one end of the wire 33 is pushed toward the bendable unit side of the endoscope 1, and the other end of the wire 33 is pulled toward the proximal end side of the operation unit 4. Thus, the two wires 12 are moved in the opposite directions, thereby the bendable unit 2 being bent.

It should be noted that, according to the embodiment, in combination of one operation dial and a pair of operation wires, the bendable portion 2 of the endoscope is bent in two directions. It is possible to use a pair of such combinations, so that the bendable portion 2 is bent in four directions.

FIG. 17 is a cross section taken along line A—A of FIG. 15. In this embodiment, end portions, on the bendable unit side, of the guide coils 29 and the inner surface of the metal connector 41 are melted so that connection portions 15 are formed. The connection portions 15 are formed by exposing these portions to arc columns.

FIG. 18 shows when the connection portions 15 are formed to connect the guide coils 29 to the metal connector 41. As shown in FIG. 18, on the metal connector 41, connection holes 41a are formed, and the guide coils 29 are located at the connection holes 41a, contacting the inner surface of the metal connector 41. Further, a first electrode 301 is inserted in the metal connector 41 and is contacted with one of the guide coils 29. A second electrode 302 is located outside the metal connector 41, in the vicinity of the connection hole 41a. For preventing the oxidization of the connection portions, an area surrounding the second electrode 302 is filled with Argon gas.

By applying a predetermined power between the first and second electrodes 301 and 302, an arc column 303 is generated between the second electrode 302 and the connection hole 41a that is located close to the second electrode 302. Since the temperature of the arc column is 5000K or more, the edge portion of the connection hole 41a and a portion of the guide coil 29 corresponding to the connection hole 41a are melted. When the power supply is terminated, and the arc column disappears, the melted metal is cooled down to the solidifying point. As a result, the tip of the guide coil 29 and the inner surface of the metal connector 41 are firmly connected.

With this structure, the connection portions 15 are formed as a slightly concaved portion with respect to the outer surface of the metal connector 41. Thus, the metal connector 41 can be smoothly inserted in the bendable unit 2.

FIG. 19 shows a cross-sectional view taken along line B—B of FIG. 18. As shown in FIG. 19, for one guide coil 29, a plurality of connection holes 41a are formed, and therefore one guide coil 29 is connected to the inner surface of the metal connector 41 at a plurality of portions (three, in this embodiment). With this structure, even if one of the connection positions 15 is disabled (released), there still remains two connection portions, and therefore, the guide coil 29 is connected to the metal connector 41 sufficiently firmly.

Sixth Embodiment

FIG. 20 shows a side view of a cleaning brush 51 for cleaning the instrument channel of the endoscope, according to a sixth embodiment. The cleaning brush 51 includes a brush unit 54 made of synthetic resin. The brush unit 54 is secured to an operation wire 52. As shown in FIG. 20, the tip of the operation wire 52 is formed to have a spherical shape 52a. A portion of the operation wire 52 on the proximal end side of the brush unit 54 is covered with a coil 53.

FIG. 21 shows the process for forming the spherical portion 52a at the tip of the operation wire 52. As shown in FIG. 21, a first electrode 301 is connected to the coil 53, and a second electrode 302 is located in the vicinity of the tip end of the operation wire 52. For preventing the oxidization of the tip end of the wire 52, an area surrounding the tip end of the wire 52 and the second electrode 302 is filled with Argon gas.

When a predetermined power is supplied between the first and second electrodes 301 and 302, an arc column is generated between the tip 52a of the wire 52 and the second electrode 302. Since the temperature of the arc column is 5000K or more, the tip 52a of the wire 52 is melted, and formed to be spherical due to its surface tension. Then, when the power supply is terminated and the arc column disappears, the tip 52a is cooled to its solidifying point. As a result, the tip 52a of the wire 52 is cured.

In the above-described embodiment, in order to form the tip 52a of the wire 52 as a spherical shape, the tip 52a is exposed to the arc column. Another method for selectively heating a small area can be applied instead of the above-described method. For example, by emitting a laser beam to the tip 52a of the wire 52, it is also possible to melt the tip 52a and form the portion as a spherical shape.

According to the above-described method to form the tip of the wire in a spherical shape, the brush instrument which does not scratch the inner surface of the channel and/or hurt the human tissues can be manufactured easily. Further, according to this method, since the collar is not used, the number of elements is reduced. Furthermore, no soldering process is required, and therefore, cleaning with fluxes is not necessary, which significantly simplifies the manufacturing process. Accordingly, the brush instrument for the endoscope can be manufactured at a low manufacturing cost.

Seventh Embodiment

FIG. 22 shows a brush instrument 51A according to a seventh embodiment of the invention. In this embodiment, instead of forming the tip 52a of the wire 52 in a spherical shape, a collar 55 is used. As shown in FIG. 22, the tip end 52a of the wire 52 is inserted in the collar 55. Then, the distal end portion 52a of the wire 52 and the distal end portion 55a of the collar 55 are exposed to the arc column. Then, the distal end portions 52a and 55a of the wire 52 and the collar 55 are melted and formed to be a hemispherical shape due to the surface tension.

According to the seventh embodiment, the collar 55 is melted to form the hemispherical (or curved) portion at the distal end thereof. Therefore, a radius of the curvature of the hemisphere is greater than the radius of the spherical portion formed in accordance with the sixth embodiment. Accordingly, the brush instrument according to the seventh embodiment causes less damage than the brush instrument according to the sixth embodiment.

Although the sixth and seventh embodiments are described in relation to the cleaning brush, another brush instrument (e.g., cytological brush instrument) which may not hurt the inner wall of the human cavity can also be manufactured in the similar manner.

Eighth Embodiment

FIGS. 23 and 24 show cross-sectional views of a part of the biopsy forceps shown in FIG. 2, according to an eighth embodiment. As shown in FIG. 24, on the cylindrical portion 203c of the supporting member 203, a plurality of through holes 203d, which are circular holes, are formed. The plurality of through holes 203d are arranged in the circumferential direction. In this embodiment, the inner diameter of the cylindrical portion 203c is substantially the same as the outer diameter of the coil 213, and the distal end portion of the coil 213 is fitted in the cylindrical portion 203c of the supporting member 203.

FIG. 25 shows how the supporting member 203 and the coil 213 is connected. As shown in FIG. 25, a first electrode 301 is connected to the coil 213. In the vicinity of the though hole 203d, a second electrode 302 is provided. It should be noted that the second electrode 302 is a cylindrical member having substantially the same diameter as the through hole 203d. Further, the second electrode 302 is arranged such that the central axis of the second electrode 302 is substantially the same as the central axis of the through hole 203d. Furthermore, in order to prevent the oxidization of the through hole 203d, an area surrounding the second electrode 302 and the through hole 203d is filled with Argon gas.

By applying a predetermined voltage between the first and second electrodes 301 and 302, an arc column 303 is generated between the through hole 203d and the second electrode 302. Since the temperature of the arc column 303 is 5000K or more, the edge portion defining the through hole 203d and a portion of the outer surface of the coil 213 corresponding to the through hole 203d are melted to form a connection portion 215. It should be noted that the arc column is generated on a line connecting the second electrode 302 and the through hole 203d closest to the second electrode 302. Thereafter, when the power supply to the first and second electrodes 301 and 302 is terminated, the arc column disappears, and the connection portion 215 is cooled down to the solidifying point. As a result, the coil 213 and the supporting member 203 are firmly connected at the portion where the through holes 203d are formed, as shown in FIG. 23.

It should be noted that the heated portion is limited to the portion exposed to the arc column, that is, the edge of the through hole 203d and the corresponding portion of the coil 213. Thus, by adjusting the duration of time during which the predetermined voltage is applied between the first and second electrodes 301 and 302 so that the inside portion of the coil 213 is not melted (e.g., a few milliseconds), is becomes possible to connect the supporting member 203 with the outer surface of the coil 213. Further, to the adjoining areas, radiant heat is conducted. Accordingly, temperature gradient between the welded portion and the adjoining portion can be suppressed relatively low. Thus, the adjoining areas will not be damaged due to heat distortion or the like.

In the above-described embodiment, the shape of the through hole 203d is a circle. However, the invention is not limited to this configuration, and the through hole 203d may have an ellipse shape. In such a case, the connecting force between the supporting member and the coil may be increased.

Ninth Embodiment

FIG. 26 shows a side view of a cleaning brush 61 according to a ninth embodiment.

As shown in FIG. 26, a brush unit 54 is secured to the distal end portion of an operation wire 52. The wire 52 on the operation unit side (right-hand side in FIG. 26) is covered with a cover coil 53 which reinforces the operation wire 52. It is preferable that a distance between the brush unit 54 and the brush unit side end of the cover coil 53 is as small as possible in view of the reinforcing function.

According to the ninth embodiment, the end portion of the cover coil 53 is connected to the operation wire 52. Specifically, the end portion of the cover coil 53 and the corresponding portion of the operation wire 52 are exposed to an arc column so that the portions of the cover coil 53 and the operation wire 52 are melted, and then hardened to form connection portions 65.

FIG. 27 shows how the cover coil 53 is connected to the operation wire 52. As shown in FIG. 27, a first electrode 301 is connected to the cover coil 53, while a second electrode 302 is placed in the vicinity of the tip end of the cover coil 53. In order to prevent oxidization of the tip of the cover coil 53, an area around the tip of the cover coil 53 and the second electrode 302 is filled with Argon gas.

By applying a predetermined voltage between the first and second electrodes 301 and 302, an arc column 303 is generated between the tip end of the cover coil 53 and the second electrode 302. Since the temperature of the arc column is 5000K or more, the tip of the cover coil 53 and a portion of the operation wire 52 contacting the tip of the cover coil 53 are melted to form the connection portions 65. It should be noted that the arc column 303 is generated on a line connecting the second electrode 302 and the closest portion of a member (i.e., the cover coil 53) connected to the first electrode 301. Therefore, in order to heat the tip of the coil 53, it is only necessary to locate the tip of the cover coil 53 at a position close to the second electrode 302, and fine adjustment thereof is unnecessary. Thereafter, the power supply is terminated, thereby the arc column disappears. Then, the connection portion 65 is cooled and solidified. In the embodiment, the connection portion 65 extends over the circumference of the tip of the cover coil 53. Alternatively, a plurality of connection portions arranged at certain intervals along the circumference of the tip of the cover coil 53 may be formed.

Tenth Embodiment

FIG. 28 shows another method of exposing the tip of the cover coil 53 to the arc column, according to a tenth embodiment. In this embodiment, instead of the first electrode 301 in the ninth embodiment, another electrode 306 formed with a nozzle 306a is used. The electrode 306 is located in the vicinity of the second electrode 302. By applying a predetermined electrical power between the electrodes 302 and 306, an arc column 303a is emitted from the nozzle 306a. Using the thus generated arc column 303a, the tip of the cover coil 53 may be melted as in the ninth embodiment.

It should be noted that a method of heating and melting the tip of the cover coil 53 is not limited to the above-described methods. Any method which is capable of heating a predetermined minute area selectively can be utilized. For example, by emitting a laser beam to the tip of the cover coil 53, the similar effect can be achieved.

According to the ninth and tenth embodiments, a brush instrument which is configured such that the connection portion 65 is as small as possible can be manufactured easily. Further, according to the ninth and tenth embodiment, since soldering process is not performed, it is unnecessary to clean elements with fluxes, which simplifies the manufacturing process. Since the distance between the brush unit and the tip end of the cover coil can be made as small as possible, the wire 52 will not be bent easily.

In the ninth and tenth embodiments, the manufacturing process of the cleaning brush instrument are described. However, the invention is not limited to the cleaning brush, and any other brush instrument such as a cytological brush instrument can be manufactured in the similar manner.

Eleventh Embodiment

FIG. 29 is a partially cross-sectional side view of a part of a cleaning brush instrument 51 according to an eleventh embodiment.

According to the eleventh embodiment, a portion 53a next to a tip end portion 53b, which is a few millimeters long, of the cover coil 53 is configured to have a wider pitch of the wound wire than the other portion to form an interstice portion. Then, at the interstice portion 53a, the coil 53 and the wire 52 are melted so that a connection portion 65 is formed, where the wire 52 and the coil 53 are connected. With this structure, since the tip end portion 53b of the coil 53 is not connected to the wire 53, and retains the elasticity, the portion of the wire 52 next to the brush unit 54 can be elastically reinforced by the cover coil 53.

According to this embodiment, in order to melt the coil 53 and the wire 52, the interstice portion 53a is exposed to an arc column.

FIG. 30 shows a procedure for forming the connection portion 65. As shown in FIG. 30, a first electrode 301 is connected to the cover coil 53, and a second electrode 302 is positioned in the vicinity of the interstice portion 53a. In order to prevent the oxidization, an area surrounding the interstice portion 53a and the second electrode 320 is filled with Argon gas.

By applying a predetermined voltage between the first and second electrodes 301 and 302, an arc column 303 is generated between the interstice portion 53a and the second electrode 302. Since the temperature of the arc column is 5000K or more, the coil 53 at the interstice portion 53a and the surface of the wire 52 located at the interstice portion 53a are melted. It should be noted that the arc column 303 is generated on a line connecting a portion of the member, which is connected to the first electrode 301 (i.e., the cover coil 53) and closest to the second electrode 302, and the second electrode 302. Thus, in order to heat the interstice portion 53a, it is only necessary to locate the interstice portion 53a closest to the second electrode 302. After the coil 53 and the corresponding portion of the wire 52 are melted, the power supply is terminated. Then, the arc column disappears, and the connection portion 65 is cooled down, thereby the connection portion 65 is solidified. By turning the coil 53 and repeating the above procedure, the entire circumference of the connection portion 65 can be solidified.

Twelfth Embodiment

FIG. 31 shows another method of exposing the interstice portion 53a to the arc column, according to a twelfth embodiment. In this embodiment, instead of the first electrode 301 in the eleventh embodiment, another electrode 306 formed with a nozzle 306a is used. The electrode 306 is located in the vicinity of the second electrode 302. By applying a predetermined electrical power between the electrodes 302 and 306, an arc column 303a is emitted from the nozzle 306a. Using the thus generated arc column 303a, the coil 53 and the surface of the wire 52 at the interstice portion 53a are melted as in the eleventh embodiment.

It should be noted that a method of heating and melting the interstice portion 53a is not limited to the above-described methods. Any method which is capable of heating a predetermined minute area selectively can be utilized. For example, by emitting a laser beam to the interstice portion 53a, the similar effect can be achieved.

According to the eleventh and twelfth embodiments, a brush instrument which is configured such that the connection portion 65 is as small as possible can be manufactured easily. Further, according to these embodiments, since soldering process is not performed, it is unnecessary to clean elements with fluxes, which simplifies the manufacturing process. Since the distance between the brush unit and the tip end of the cover coil can be made as small as possible, the wire 52 will not be bent easily.

In the eleventh and twelfth embodiments, the manufacturing process of the cleaning brush instrument are described. However, the invention is not limited to the cleaning brush, and any other brush instrument such as a cytological brush instrument can be manufactured in the similar manner.

Thirteenth Embodiment

FIG. 32 shows a tip end portion of a cytological brush instrument 61 according to a thirteenth embodiment.

As shown in FIG. 32, the cytological brush instrument 61 has an operation wire 52, which is covered with a cover coil 53. In order to prevent relative movement between the operation wire 52 and the cover coil 53, the wire 52 and the coil 53 are connected at the tip ends thereof. According to the embodiment, the tip portion of the cytological brush instrument 61 is exposed to an arc column so that the wire 52 and the coil 53 are melted at the tip portion thereof.

A manufacturing process will be described hereinafter. Firstly, the wire 52 is inserted through the coil 53, and as show in FIG. 32, a tip end portion (a few millimeters long) is protruded from the end of the cover coil 53. Then, as shown in FIG. 32, a first electrode 301 is connected to the cover coil 53, and a second electrode 302 is located in the vicinity of the tip of the wire 52. In order to prevent the oxidization of the tip end 53a of the coil 53, an area surrounding the tip end 53a of the coil 53 and the second electrode 302 is filled with Argon gas.

By applying a predetermined voltage between the first and second electrodes 301 and 302, the arc column 303 is generated between the second electrode 302 and the tip 52a of the wire 52. Since the temperature of the arc column 303 is 5000K or more, The tip 52a of the wire 52 and the tip 53a of the coil 53 are melted to form a connection portion 55.

It should be noted that the arc column 303 is generated on a line connecting the second electrode 302 and a portion of a member which is connected to the first electrode 301 and closest to the second electrode 302. Therefore, in order to heat the tip 52a of the wire 52, it is only necessary to locate the tip 52a of the wire 52 closest to the second electrode 302, and no further fine positioning procedure is necessary.

After the tip 52a of the wire 52 and the tip 53a of the coil 53 are exposed to the arc column 303 and are melted, the power supply is terminated. Then, the connection portion 55 is cooled and solidified, as shown in FIG. 34.

Fourteenth Embodiment

FIG. 35 shows another method of exposing the tip of the wire 52 to the arc column, according to a fourteenth embodiment. In this embodiment, instead of the first electrode 301 in the thirteen embodiment, another electrode 306 formed with a nozzle 306a is used. The electrode 306 is located in the vicinity of the second electrode 302. By applying a predetermined electrical power between the electrodes 302 and 306, an arc column 303a is emitted from the nozzle 306a. Using the thus generated arc column 303a, the tip of the operation wire 52 may be melted as in the thirteen embodiment.

It should be noted that a method of heating and melting the tip of the operation wire 52 is not limited to the above-described methods. Any method which is capable of heating a predetermined minute area selectively can be utilized. For example, by emitting a laser beam to the tip of the operation wire 52, the similar effect can be achieved.

According to the thirteenth and fourteenth embodiments, a brush instrument which is configured such that the connection portion 55 is as small as possible can be manufactured easily. Further, according to the thirteenth and fourteenth embodiment, since soldering process is not performed, it is unnecessary to clean elements with fluxes, which simplifies the manufacturing process. Since the distance between the brush unit and the tip end of the cover coil can be made as small as possible, the wire 52 will not be bent easily.

In the thirteenth and fourteenth embodiments, the manufacturing process of the cytological brush instrument are described. However, the invention is not limited to the cytological brush, and any other instrument, which includes a wire and a device to be operated, such as a cleaning brush instrument can be manufactured in the similar manner.

The present disclosure relates to the subject matters contained in Japanese Patent Applications No. 2000-244491, filed on Aug. 11, 2000, No. 2000-265124, filed on Sep. 1, 2000, No. 2000-328675, filed on Oct. 27, 2000, No. 2000-328911, filed on Oct. 27, 2000, No. 2000-329039, filed on Oct. 27, 2000, No. 2000-365831, filed on Nov. 30, 2000, No. 2000-391556, filed on Dec. 22, 2000, and No. 2000-391659, filed on Dec. 22, 2000, which are expressly incorporated herein by reference in their entireties.

What is claimed is:

1. A method of manufacturing a treatment instrument of an endoscope, said treatment instrument including a first coil and a second coil that is different from said first coil and to be connected to said first coil, an operation wire, and a device secured to a distal end of said first coil, said wire being inserted through said first coil and said second coil, a distal end of said wire being connected to said device, said device being driven by said wire when said wire is moved in said first coil and said second coil, said method comprising:

inserting one end of said first coil and one end of said second coil in a connection pipe from opposite ends thereof; and exposing ends of said connection pipe and portions of said first coil and said second coil corresponding to said ends of said connection pipe to arc columns, respectively, the portions exposed to the arc columns being melted, and thereafter, solidified.

2. The method according to claim 1, wherein an outer diameter of said connection pipe is substantially the same as an outer diameter of said first coil outside said connection pipe and an outer diameter of said second coil outside said connection pipe, and wherein an inner diameter of said connection pipe is substantially the same as an outer diameter of said first coil inside said connection pipe and an outer diameter of said second coil inside said connection pipe.

3. The method according to claim 1, wherein a plurality of positions, along a circumferential direction, of a portion where an end of said connection pipe is to be connected to said first coil are exposed to arc columns, respectively, and wherein a plurality of positions, along a circumferential direction, of a portion where an other end of said connection pipe is to be connected to said second coil are exposed to arc columns, respectively.

4. The method according to claim 1, wherein said connection pipe is formed with a plurality of through holes, each of which is exposed to an arc column, whereby an edge portion of each of said through holes and one of said first and second coils located at each of said through holes are heated and melted.

5. A method of manufacturing a treatment instrument of an endoscope, said treatment instrument including a first coil and a second coil that is different from said first coil and to be connected to said first coil, an operation wire, and a device secured to a distal end of said first coil, said wire being inserted through said first coil and said second coil, a distal end of said wire being connected to said device, said device being driven by said wire when said wire is moved in said first coil and said second coil, said method comprising generating an arc column between a contact portion where a proximal end side of said first coil and a distal end side of said second coil contact with each other and an electrode located in the vicinity of the contact portion, the proximal end side of said first coil and the distal end side of said second coil located at the contact portion being melted as exposed to the arc column, and solidified as cooled.

6. The method according to claim 5,
wherein a plurality of positions, along a circumferential direction, of the contact portion are exposed to arc columns, respectively.

7. The method according to claim 5, wherein said first coil includes a flexible coil, and wherein said second coil includes a rigid coil.

8. A method of manufacturing a treatment instrument of an endoscope, said treatment instrument including a first guide coil, an operation wire, and a device to be operated, said wire being inserted through said first guide coil, a distal end of said wire being connected to said device, said device being driven by said wire when said wire is moved in said first guide coil, said method comprising:

inserting said first guide coil into a first cover coil; and exposing a plurality of portions of said first cover coil at positions where said first cover coil covers said first guide coil to arc columns, respectively, said first cover coil and said first guide coil at portions exposed to the arc columns being melted, and thereafter, solidified.

9. The method according to claim 8, wherein the exposing includes:

locating an electrode at each of the plurality of portions; and applying a predetermined voltage between said first cover coil and said electrode to generate the arc column therebetween.

10. The method according to claim 8, wherein said instrument is a biopsy forceps having a pair of cups that is opened and closed by operation of said operation wire.

11. A method of manufacturing an endoscope, said endoscope including a first guide coil, and an operation wire, said wire being inserted through said first guide coil, a distal end portion of said endoscope being provided with a moving mechanism, a distal end of said wire being connected to said moving mechanism, said moving mechanism being driven by said wire when said wire is moved in said first guide coil, said method comprising:

inserting said first guide coil into a first cover coil; and exposing a plurality of portions of said first cover coil at positions where said first cover coil covers said first guide coil to arc columns, respectively, said first cover coil and said first guide coil at portions exposed to the arc columns being melted, and thereafter, solidified.

12. The method according to claim 11, wherein the exposing includes:

locating an electrode at each of the plurality of portions; and applying a predetermined voltage between said first cover coil and said electrode to generate the arc column therebetween.

13. A method of manufacturing an endoscope, said endoscope including an insertion tube to be inserted in a human cavity, a bendable unit provided on a distal end side of said insertion tube, said bendable unit being operated by a pair of operation wires, and a connection member that connects said insertion tube with said bendable unit, said connection member having substantially a cylindrical shape, said method comprising:

positioning a guide coil that covers said operation wire to elastically reinforce so that a bendable unit side end of said guide coil contacts an inner surface of said connection member; and exposing said connection member to an arc column so that the connection member and the outer surface of said guide coil is heated and melted.

14. The method according to claim 13,
wherein at least one through hole is formed on a side surface of said connection member,
wherein the exposing includes:
positioning a tip end portion of said guide coil at said at least one through hole, and
exposing the at least one through hole to an arc column to melt the connection member and the guide coil at a position corresponding to the at least one through hole.

15. The method according to claim 13,
wherein a plurality of through holes are formed on a side surface of said connection member, said plurality of though holes being aligned in an axial direction of the connection member, and
wherein the exposing includes:
positioning a tip end portion of said guide coil at said plurality of through holes, and
exposing the plurality of through holes to an arc column to melt said connection member and said guide coil at positions corresponding to said plurality of through holes.

16. The method according to claim 15, wherein said exposing comprises:

connecting an electrode to said guide coil;
locating another electrode in the vicinity of at least one of said though holes; and
applying a predetermined voltage between said electrode and said another electrode to generate an arc column therebetween.

17. A method of manufacturing a brush instrument for an endoscope, said brush instrument including a brush unit and an operation wire, said brush unit being secured to a distal end portion of said operation wire, said method comprising:

heating a tip of said wire so that the tip of said operation wire is melted, a substantially hemispherical portion being formed thereat; and cooling the melted portion of said operation wire.

18. The method according to claim 17, wherein said heating comprises exposing the tip of said operation wire to an arc column.

19. The method according to claim 17, wherein said heating comprises exposing the tip of said operation wire to a laser beam.

20. A method of manufacturing a brush instrument for an endoscope, said brush instrument including a brush unit and an operation wire, said brush unit being secured to a distal end portion of said operation wired wire, said method comprising:

inserting a tip end of said operation wire in a collar member, said operation wire protruding from an end of said collar by a predetermined amount, heating a tip of said operation wire protruding from said collar so that the tip of said operation wire is melted, a substantially hemispherical portion being formed by the melted portion of said operation wire; and cooling the melted portion of said operation wire.

21. The method according to claim 20, wherein said heating comprises exposing said tip of said operation wire to an arc column.

22. The method according to claim 20, wherein said heating comprises exposing said tip of said operation wire to a laser beam.

23. A method of manufacturing a treatment instrument for an endoscope, said instrument including an operable member protruding from a distal end of said endoscope, said operable member being driven by moving an operation wire inserted in said endoscope, said method comprising:

securing said operable member onto a support member that restricts movement of said operable member;

covering said operation wire with a coil;

connecting a tip end of said coil and said supporting member by arc welding.

24. The method according to claim 23, wherein said supporting member has a cylindrical portion, an inner diameter of said cylindrical portion being substantially the same as an outer diameter of said coil, and wherein said arc welding is performed while inserting the tip end of said coil in said cylindrical portion.

25. The method according to claim 24, wherein said cylindrical portion is formed with at least one through hole extending in a radial direction, and wherein the tip end of said coil and said supporting member are connected by welding at a position where said at least one through hole is formed.

26. The method according to claim 25, wherein said at least one through hole includes a plurality of through holes spaced in a circumferential direction.

27. The method according to claim 23, wherein said treatment instrument includes a forceps provided with a pair of forceps cups.

28. A method of manufacturing a treatment instrument for an endoscope, said treatment instrument including a brush unit, and brush an operation wire, said brush being secured to a distal end portion of said operation wire, said wire being covered with a coil, said method comprising:

heating a tip of said wire so that the tip of said operation wire and a tip of said coil are melted and connected; and cooling the melted portion of said operation wire and said coil.

29. The method according to claim 28, wherein said heating comprises exposing said tip of said operation wire and coil to an arc column.

30. The method according to claim 28, wherein said heating comprises exposing said tip of said operation wire and coil to a laser beam.

31. A method of manufacturing a treatment instrument for an endoscope, said treatment instrument including a treatment unit and an operation wire, said treatment unit being secured to a distal end portion of said operation wire, said wire being covered with a coil at a portion on a proximal end side with respect to said treatment unit, said method comprising:

widening a pitch of said coil at a position a predetermined length spaced from a tip end of said coil to form an interstice portion;

heating said coil and said wire at said interstice portion so that said coil and the corresponding portion of said operation wire are melted and connected; and cooling the melted portion of said operation wire and said coil.

32. The method according to claim 31, wherein said heating comprises exposing said interstice portion of said coil and the corresponding portion of said operation wire to an arc column.

33. The method according to claim 31, wherein said heating comprises exposing said interstice portion of said coil and the corresponding portion of said operation wire to a laser beam.

34. The method according to claim 31, wherein said treatment unit includes a brush unit.

* * * * *